United States Patent
Burns et al.

(10) Patent No.: US 7,188,515 B2
(45) Date of Patent: Mar. 13, 2007

(54) NANOLITER VISCOMETER FOR ANALYZING BLOOD PLASMA AND OTHER LIQUID SAMPLES

(75) Inventors: Mark A. Burns, Ann Arbor, MI (US); Nimisha Srivastava, Ann Arbor, MI (US); Robertson D. Davenport, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/235,641

(22) Filed: Sep. 26, 2005

(65) Prior Publication Data

US 2006/0179923 A1    Aug. 17, 2006

Related U.S. Application Data

(60) Provisional application No. 60/613,188, filed on Sep. 24, 2004.

(51) Int. Cl.
*G01N 11/04* (2006.01)

(52) U.S. Cl. .............. 73/54.05; 73/54.04; 73/54.07; 73/54.09; 73/54.13; 702/50

(58) Field of Classification Search .............. 73/54.07, 73/54.09, 54.04, 54.05, 54.13; 702/50
See application file for complete search history.

(56) References Cited

U.S. PATENT DOCUMENTS

| | | | |
|---|---|---|---|
| 5,847,268 A * | 12/1998 | Ball | 73/54.09 |
| 6,322,524 B1 | 11/2001 | Kensey et al. | |
| 6,402,703 B1 | 6/2002 | Kensey et al. | |
| 6,412,336 B2 | 7/2002 | Shin et al. | |
| 6,428,488 B1 | 8/2002 | Kensey et al. | |
| 6,484,565 B2 | 11/2002 | Shin et al. | |
| 6,523,396 B2 | 2/2003 | Shin et al. | |
| 6,571,608 B2 | 6/2003 | Shin et al. | |
| 6,624,435 B2 | 9/2003 | Kensey et al. | |
| 6,681,616 B2 | 1/2004 | Spaid et al. | |
| 6,732,573 B2 | 5/2004 | Shin et al. | |
| 6,732,574 B2 | 5/2004 | Hajduk et al. | |
| 6,745,615 B2 | 6/2004 | Kensey et al. | |
| 6,990,851 B2 | 1/2006 | Spaid et al. | |
| 7,040,144 B2 * | 5/2006 | Spaid et al. | 73/54.05 |
| 2002/0148282 A1 * | 10/2002 | Hajduk et al. | 73/54.07 |
| 2003/0041652 A1 * | 3/2003 | Spaid et al. | 73/54.05 |
| 2003/0182991 A1 * | 10/2003 | Spaid et al. | 73/54.04 |

OTHER PUBLICATIONS

"An Optical Micro-Fluidic Viscometer", Paul Galambos & Fred Forster, DSC-vol. 66, Micro-Electro-Mechanical System (MEMS), 1998, pp. 187-191.

(Continued)

*Primary Examiner*—Hezron Williams
*Assistant Examiner*—Samir M. Shah
(74) *Attorney, Agent, or Firm*—Brooks Kushman P.C.

(57) ABSTRACT

A microfabricated, a nanoliter capillary viscometer includes a first channel that is defined by a first channel-defining surface in a first substrate and a second channel defining surface in a second substrate. The progress of liquid through this first channel is monitored and used to determine viscosity. Viscosities in the range of 1 cP to 1000 cP are easily measured. Self-calibrating versions of the viscometer are also disclosed.

23 Claims, 22 Drawing Sheets

OTHER PUBLICATIONS

"A Differential Viscosity Detector for Use in Miniaturized Chemical Separation Systems", Marko T. Blum et al., Journal of Microelectromechanical Systems, vol. 14, No. 1, Feb. 2005, pp. 70-80.

Micromachined Viscosity Sensor for Real-Time Polymerization Monitoring, Oliver Brand et al., TRANSDUCERS '97, 1997 International Conference on Solid-State Sensors and Actuators, Chicago, Jun. 16-19, 1997, pp. 121-124.

"Measurement of Temperature and Liquid Viscosity Using Wireless Magneto-Acoustic/Magneto-Optical Sensors", M.K. Jain et al., IEEE Transaction on Magnetics, vol. 37, No. 4, Jul. 2001, pp. 2767-2769.

"Intrinsic Viscosity of Polymers and Biopolymers Measured by Microchip", Jinkee Lee & Anhubhav Tripathi, Analytical Chemistry, vol. 77, No. 22, Nov. 15, 2005, pp. 7137-7147.

"Viscosimeter on a Microfluidic Chip", Pierre Guillot et al., LANGMUIR 2006, 22, pp. 6438-6445.

Oscillating Viscometer—Evaluation of a new Bedside Test, M. Mark et al., BIORHEOLOGY, 43 (2006), pp. 133-146.

* cited by examiner

NANOLITER VISCOMETER FOR ANALYZING BLOOD PLASMA AND OTHER LIQUID SAMPLES

CROSS-REFERENCE TO RELATED APPLICATIONS

This application claims the benefit of U.S. Provisional Application Ser. No. 60/613,188 filed Sep. 24, 2004; the entire disclosure of which is hereby incorporated by reference.

STATEMENT REGARDING FEDERALLY SPONSORED RESEARCH OR DEVELOPMENT

The invention was made with Government support under Contract No. HG01984. The Government has certain rights to the invention.

BACKGROUND OF THE INVENTION

1. Field of the Invention

The present invention relates to miniaturized viscometers and in particular to miniaturized viscometers capable of measuring the viscosity of nanoliter sized liquid samples.

2. Background Art

Measuring the viscosity of chemical and biological fluids is an important analytical tool in applications ranging from medical diagnostics and research to the chemical and manufacturing industry. In the paints industry, viscosity measurements aid in characterizing the fabrication and thickness of paints, varnishes, and coatings. Similarly, characterizing the viscosity of inks helps in ensuring uniform print and avoidance of smearing in both offset and ink-jet printing. In polymer rheology, intrinsic viscosity is widely used to measure the molecular weight of polymers, and the viscosity of melts and solutions is essential in designing processes such as injection molding and extrusion. The viscosity of biological solvents helps in gaining insight into the kinetics and dynamics of molecular and cellular processes such as conformational changes in protein. In addition, the viscosity of body fluids such as blood, blood plasma, amniotic, and synovial fluid plays an important role in diagnostic, prognostic, and preventive medicine.

Two commonly used viscometers are the cone and plate viscometer and the capillary viscometer. In the cone and plate viscometer, liquid is sheared between an inverted rotating cone and a stationary flat plate and the torque required to turn the cone at a known angular velocity determines the viscosity. While comparatively expensive, the cone and plate viscometer allows analysis of all aspects of rheological behavior. In capillary viscometers, liquid is made to flow through a capillary tube under a known pressure difference and the measured rate of flow is used to calculate the viscosity. The capillary viscometer, though inexpensive and simple to use, is mostly limited to Newtonian liquids due to the fact that the velocity in the tube and, therefore, the shear rate is constant.

Most current viscometers are designed predominantly as benchtop instruments that are difficult to use at the point of sample collection. Recently, a few miniaturized viscometers that measure viscosity using low sample volume have been developed.

Accordingly, there exists a need for a viscometer that is inexpensive and that uses low sample volumes that are, in particular, suitable for biological and medical applications.

SUMMARY OF THE INVENTION

The present invention solves one or more problems of the prior art by providing in one embodiment a microfabricated, nanoliter capillary viscometer. The viscometers of this embodiment include a first channel that is defined by a first channel-defining surface in a first substrate and a second channel defining surface in a second substrate. The progress of liquid through this first channel is monitored and advantageously used to determine viscosity. Advantageously, the viscometers of the invention are microfluidic and microfabricated. Viscosity measurements using the devices of the invention are performed rapidly often in about 1 to 5 minutes. Viscosities in the range of 1 cP to 1000 cP are easily measured.

The viscometers of the present invention are manufactured using standard photolithographic methods, are easy to fabricate, have no moving parts, measures viscosity rapidly, and requires minimal sample volume. The microfabricated viscometer operates entirely through capillary pressure generated within microfluidic channels without the need for external actuation. The viscometers of the present invention are inexpensive devices and may be disposed of after each use. A wide range of shear rates may be obtained with microfabricated viscometers of the present invention by appropriately changing the geometry and dimensions of the microfluidic channels. Moreover, the microfabricated viscometers of the invention are useful for measuring the viscosity of both Newtonian and non-Newtonian fluids. In another embodiment of the invention, a self-calibrating nanoliter viscometer has been successfully tested with viscosity standards and blood plasma.

The microfabricated capillary viscometers of the present invention offer several advantages over existing viscometers. The viscometers of the present invention are easy to use. A user simply needs to place a drop of liquid at the inlet of the channel and monitor the velocity profile. While most prior art viscometers require at least a few milliliters of a liquid sample, the microfabricated viscometers of the invention requires only 1 μL or less for operation. Such a small volume is of significance to many biochemical and medical applications where limited sample volume is available. Advantageously, the total time for viscosity measurements with the viscometers of the invention is less than 1 minute compared to 1 h/sample on typical existing equipment. A microdevice incorporating multiple channels in accordance to embodiments of the present invention are able to perform simultaneous viscosity measurements thereby reducing the time taken per sample and allowing comparison between samples. Finally, the viscometers of the present invention are inexpensive to produce.

DETAILED DESCRIPTION OF THE PREFERRED EMBODIMENT(S)

Figure 1:
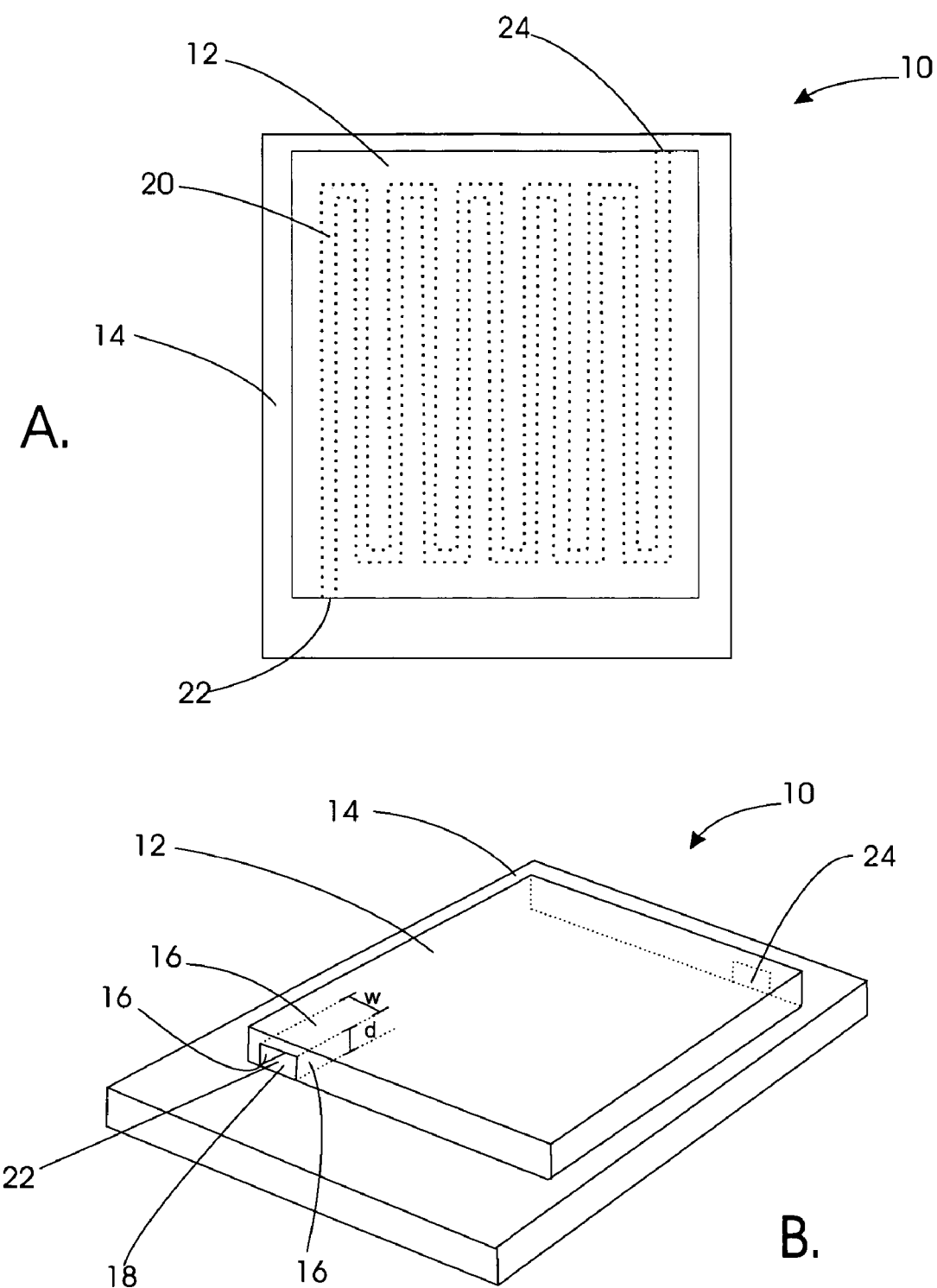
FIG. 1A is a top view of an embodiment of the viscometer of the invention.
FIG. 1B is a perspective view of an embodiment of the viscometer of the invention.

Reference will now be made in detail to the presently preferred compositions or embodiments and methods of the invention, which constitute the best modes of practicing the invention presently known to the inventors.

With reference to FIGS. 1A and 1B, illustrations of an embodiment of a viscometer of the present invention are provided. Aspects fo the present invention are described in *Nanoliter Viscometer for Analyzing Blood Plasma and Other Liquid Samples*, Anal. Chem. 2005, 77, 383–392. The entire disclosure of this publication is hereby incorporated by reference. Viscometer 10 includes first substrate 12 and second substrate 14. First substrate 12 includes first channel-defining surface 16. Similarly, second substrate 14 includes second channel-defining surface 18. First channel 20 is defined by the first channel-defining surface 16 and second channel defining surface 18. First substrate 12 and second substrate 14 may be made from any material capable of being fabricated with the required dimensions of first channel 20. Preferably the selection of material for first substrate 12 and second substrate 14 ensures that the combined contact angle is less than 90 degrees. Suitable materials include, but are not limited to, glass, ceramic, plastic, crystalline silicone wafers, and the like. In a variation, first substrate 12 is a glass plate and first channel-defining surface 16 forms a trench positioned in the glass plate and second substrate 14 is a silicon wafer. In this variation, the glass plate positioned over the silicon wafer such that the glass plate in combination with the silicon wafer define first channel 20. First channel 20 is typically serpentine (i.e., turning and reversing direction several times) in order to provide for a sufficient length through which a liquid flows to provide accurate viscosity determinations. First channel 20 includes inlet 22 for introduction of liquid into first channel 20 and outlet 24 for venting gas as liquid fills first channel 20. First channel 20 is also characterized by its dimensions of width ("w"), height ("d"), and total length ("$L_{total}$") from inlet 22 to outlet 24. In an important variation of the invention first channel 20 is a micrometer-sized channel. Although virtually any dimensions compatable with the components are possible, first channel 20 typically has a cross-sectional area from about 0.003 $mm^2$ to about 0.05 $mm^2$ and with a length from about 10 mm to about 200 mm. Viscometer 10 also includes a liquid rate measuring meter (not shown but described in more detail below) for measuring the rate at which liquid fills first channel 20. The liquid rate measuring meter includes any device capable of monitoring the rate of liquid filling first channel 20. Examples of such meters include, a video capture device that records the progress of the liquid into first channel 20 and the electrode system set forth below. The liquid rate measuring meter is in communication with first channel 20 in order to determine the rate at which liquid fills first channel 20. The viscosity of a liquid is determined from this rate as set forth below.

The calculation of viscosity with viscometer 10 is based on pressure-driven laminar flow inside micrometer-diameter-sized channels. Such flows can be approximated using the Hagen-Poiseuille flow equation:

$$v=(d^2/S\mu)(\Delta P/L) \quad (1)$$

where v is the mean velocity, d is the depth of the channel, L is the length of the liquid column inside the channel at any time, μ is the liquid viscosity, ΔP is the pressure difference across the liquid inside the channel, and S is the shape factor which is a constant specific to channel geometry (slit, S=12; circular, S=32; square, S=28.45). By rearranging eq 1, the following expression for the viscosity is obtained:

$$\mu = (d^2/S)(\Delta P/vL) \quad (2)$$

The viscosity of any liquid may be calculated once the terms on the right side of equation 2 are determined. Typically the channel dimensions are predetermined from design and fabrication. Therefore, $d^2/S$ is known or can be measured. After measuring or calculating $\Delta P$, the product vL is measured on a microchannel such as channel 20 and used to calculate the viscosity using eq 2.

Figure 2:
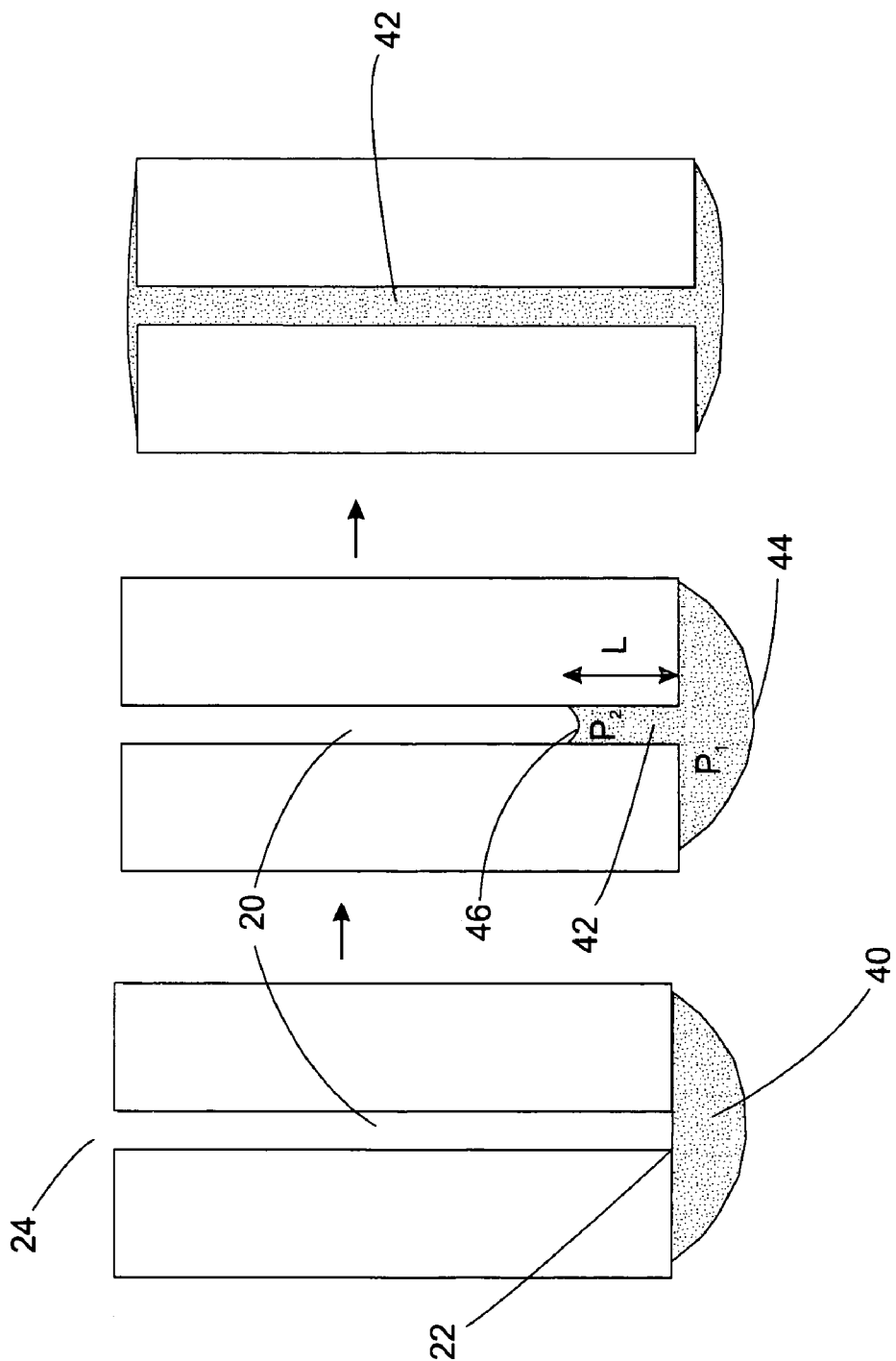
FIG. 2 is a schematic demonstrating the determination of ΔP is provided.

In one variation of the present embodiment, $\Delta P$ is determined by using capillary pressure to induce and sustain liquid motion inside channel 20. By virtue of capillary action, a drop of aqueous liquid placed at the inlet of a hydrophilic microfluidic channel is spontaneously drawn into the channel and continues to flow until it reaches the outlet. With reference to FIG. 2, a schematic demonstrating the determination of $\Delta P$ is provided. Liquid drop 40 is placed proximate to inlet 22 such that liquid is drawn into channel 20 to form a liquid column 42. At any instant, liquid column 42 contains meniscus 44 associated with a radius of curvature $R_1$ and meniscus 46 associated with a radius of curvature $R_2$. Meniscus 46 is inside microfluidic channel 20 and is associated with the channel dimensions while meniscus 44 is outside the channel and is associated with a large excess fluid. The difference in shapes of these menisci produces a differential pressure between inlet 22 and outlet 24 of the liquid column and results in movement from the high-pressure (i.e., external, $P_1$) to the low-pressure end (i.e., inside the channel, $P_2$). Since there is a large amount of excess fluid outside channel 20, it can be assumed that $R_1$ is much larger than $R_2$. The differential pressure ($\Delta P$) may be calculated from the Young-Laplace equation:

$$\Delta P = P_1 - P_2 = (P_{atm} - \sigma/R_1) - (P_{atm} - \sigma/R_2) = \sigma/R_2 \quad (3)$$

where $R_2$ is given by:

$$1/R_2 = 2\cos\theta(1/d + 1/w) \quad (4)$$

Thus, $\Delta P$ is given by $$\Delta P = P_{capillary} = 2\sigma\cos\theta(1/d + 1/w) \quad (5)$$

where $\theta$ is the contact angle, $\sigma$ is the surface tension of the liquid, and w is the width of the channel. As the liquid reaches the end of the channel, $R_2$ and $R_1$ become comparable and the liquid stops flowing.

While the liquid may experience other forces, capillary forces are the most dominant on micrometer-length scales. To illustrate this point, a series of relevant dimensionless numbers characterizing the strength of the other forces are listed in Table 1. These dimensionless numbers have been calculated for a drop of water moving at a velocity of 1 mm/s inside a 10-μm-diameter capillary at room temperature. As seen from the table, capillary forces are the strongest.

TABLE 1

| | Dimensionless Numbers | | |
|---|---|---|---|
| no. | dimensionless number | comparison of forces formula | value |
| 1 | (1/bond number (Bo)) | (surface tension force/gravitational force) ($\sigma/\rho g d^2$) | ~$10^5$ |

TABLE 1-continued

| | Dimensionless Numbers | | |
|---|---|---|---|
| no. | dimensionless number | comparison of forces formula | value |
| 2 | (1/capillary number (Ca)) | (surface tension force/viscous force) ($\sigma/\mu v$) | ~$10^5$ |
| 3 | (1/Ca, Reynolds number (Re)) | (surface tension/inertial force) ($\sigma/d\rho v^2$) | ~$10^7$ |

Figure 3A:
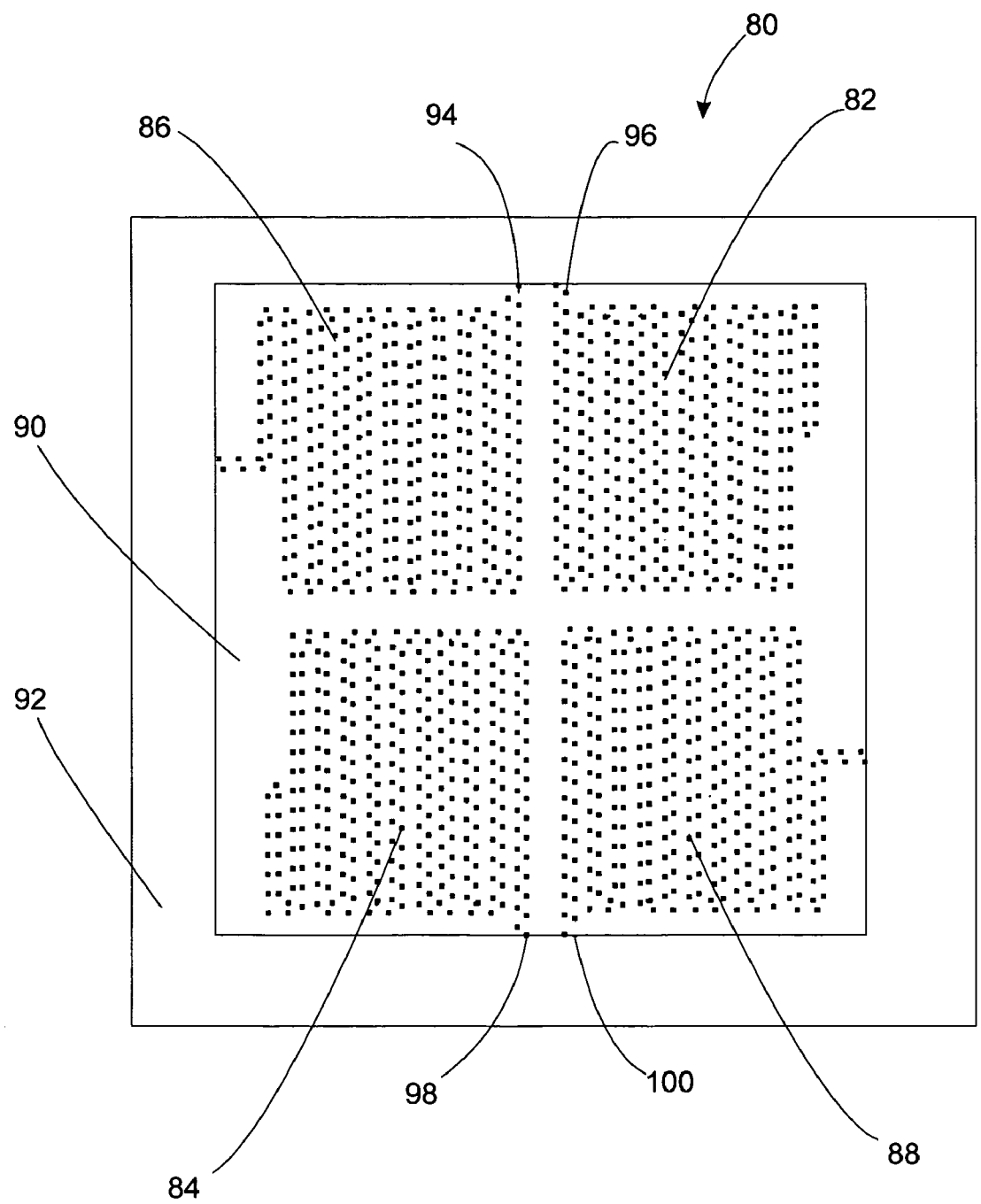
FIG. 3A is a top view of a self-calibrating viscometer.

In another embodiment of the present invention, a self-calibrating nanoliter viscometer is provided. The viscometer of this embodiment incorporates components for measuring $P_{capillary}$ and $d^2/S$. With reference to FIG. 3A, a schematic of the viscometer of this embodiment is provided. Viscometer system 80 includes four channels 82, 84, 86, 88 which together are used to measure the viscosity of a liquid sample. Channels 82, 84 are closed-end or sealed (d~45 μm, w~300 μm, $L_{total}$~9.0 cm) while channels 86, 88 are open (d~45 μm, w~300 μm, $L_{total}$~9.6 cm). The construction of channels 82, 84, 86, 88 is analogous to the construction of the channels described above. Specifically, substrates 90, 92 each include a channel-defining surface for each of channels 82, 84, 86, 88. Therefore substrates 90, 92 are attached together to define channels 82, 84, 86, 88. One set of open and sealed channels (e.g. channels 82, 86) are used for a calibration by placing a drop of liquid of known viscosity proximate to inlets 94, 96. Viscometer system 80 also includes a liquid volume meter (not shown) for measuring the amount of liquid filling closed-end channels 82, 84. The liquid volume meter includes any device capable of monitoring the amount of liquid filling closed-end channels 82, 84. Examples of such meters include, a video capture device that records the progress of the liquid into channels 82, 84 and the electrode system set forth below. A drop of a liquid sample for which viscosity is to be determined is placed proximate to inlets 98, 100. Proper design and fabrication ensures that the open channels 86, 88 are of substantially identical geometry (i.e., identical d, w, and therefore, S).

Still referring to FIG. 3A, $P_{capillary}$ is measured by placing a drop of liquid at the inlet of a sealed channel and is spontaneously drawn into the channel. Advantageously, liquid drops as small as or smaller than 5-μL can be used. Moreover, liquid volumes as low as 100 nanoliters are successfully measured. The trapped air in closed end channels 82, 84 is compressed as the liquid moves in to balance the capillary pressure difference. The air pressure inside the channel after the drop moves in and exceeds the atmospheric pressure by an amount equal to the capillary pressure. Using the ideal gas law, the capillary pressure is calculated from:

$$P_{capillary} = P_{atm}(V_1/V_2 - 1) \quad (6)$$

In Equation 6, $V_1$ is the original volume of air inside channels 82, 84 and $V_2$ is the volume of the compressed air found from the position of the air/liquid meniscus inside channels 82, 84. Such measurement of the capillary pressure is independent of the liquid or the substrate and does not require a prior knowledge of surface tension, contact angle or channel geometry.

The parameter $d^2/S$ is measured using a calibration liquid of known viscosity (e.g., water) on one set of open and sealed channels (e.g. channels 82, 86). The product, $vL_{calib}$, is calculated from open channel 86 as set forth above.

$P_{capillary,calib}$ is found from the closed channel using eq 6. The parameter $d^2/S$ is calculated from eq 1 as follows:

$$d^2/S = \mu_{calib}(vL_{calib}/P_{capillary,calib}) \quad (7)$$

where $\mu_{calib}$ is the viscosity of the calibration liquid. Since both open channels 86, 88 on viscometer 80 are of identical geometry, the calculated value of $d^2/S$ applies to each of open channels 86, 88. The viscosity is calculated using:

$$\mu_{sample} = \mu_{calib}(vL_{calib}/P_{capillary,calib})P_{capillary,sample}/vL_{sample} \quad (8)$$

Advantageously, viscosity determinations by the viscometers of the present invention are not substantially sensitive to the square turns of the channels. Significant deviations from plain Poiseuille flow are not observed thereby obviating a potential source of error. The flow of liquid at the round turns is smoother when compared to square turns. In square turns, bubbles may occasionally get trapped at the corners. A blood plasma sample tested on the round turn viscometer gave a viscosity of 1.456 (0.163 cP at 37° C. (precision 11%). When compared to the results from devices with square turns, the precision is almost identical, indicating that either channel geometry is acceptable.

Figure 3B:
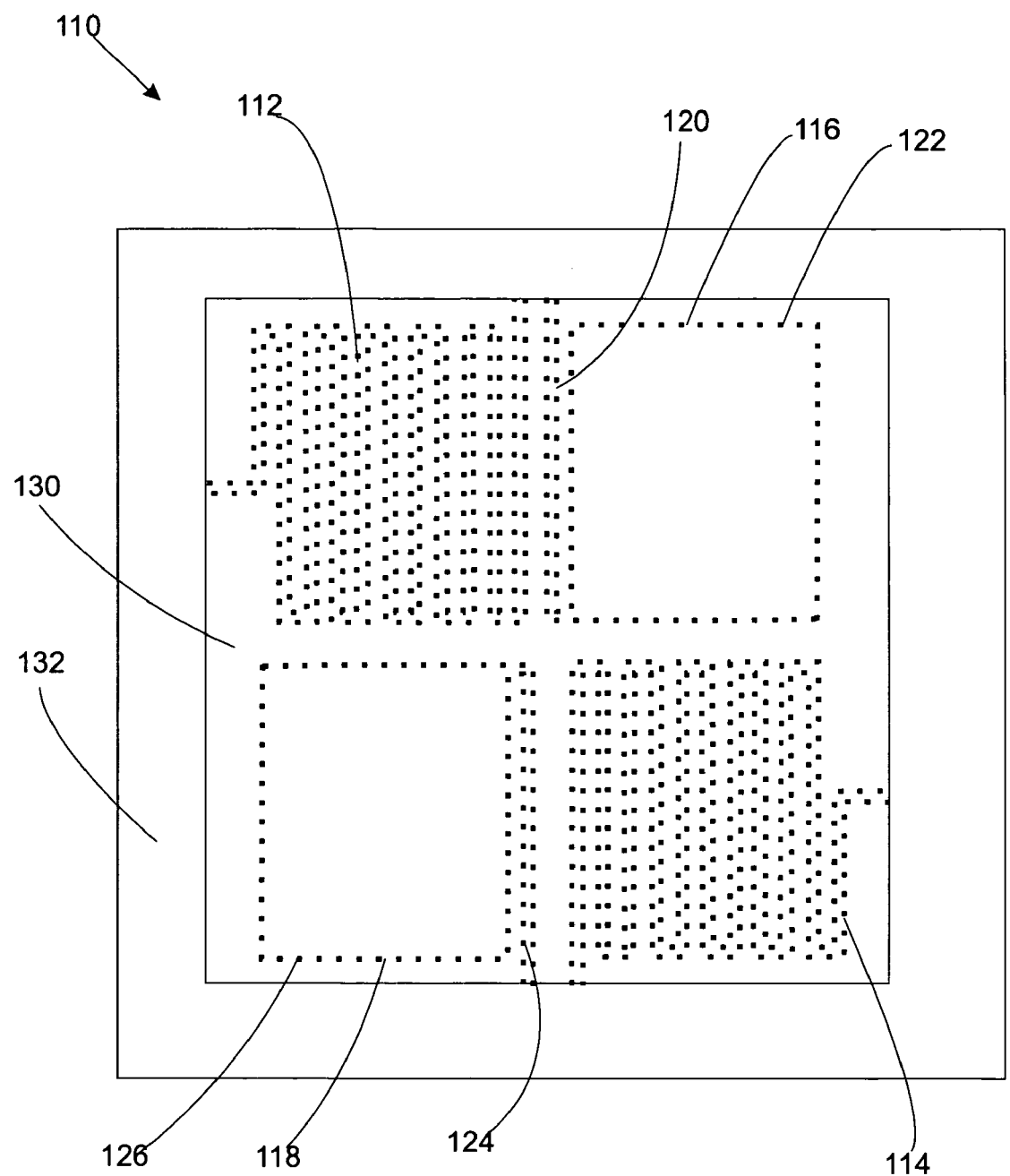
FIG. 3B is top view of a variation of a self-calibrating viscometer.

With reference to FIG. 3B, a variation of the self-calibrating design of FIG. 3A in which a portion of the sealed channels is replaced by a chamber is provided. FIG. 3B provides a schematic of the viscometer of this variation. Viscometer 110 includes open channels 112, 114 and closed conduits 116, 118. Close conduit 116 includes channel section 120 feeding into closed chamber section 122. Similarly, close conduit 118 includes channel section 124 feeding into closed chamber section 126. Again, substrates 130, 132 each includes a channel-defining surface for each of open channels 112, 114 and closed conduits 116, 118. Utilization of chambers such as chamber sections 122 and 126 provide certain advantages. For example, with a square chamber, a higher etched volume is achieved using the same area/footprint of the device by essentially eliminating the wall area between the segments of the serpentine channels. Consequently in order to achieve a certain volume $V_1$, a square chamber would use less space/footprint as compared to a channel.

In still another variation of this embodiment, the determination of the viscosity for non-Newtonian liquids is provided. It should be appreciated that the determination of viscosity for non-Newtonian liquids may not be performed simply by calculating the product vL as set forth above for Newtonian liquids. However, empirical relationships that correlate the viscosity of some non-Newtonian fluids to the mean velocity (v) and column length (L) are known. The viscosity of a non-Newtonian liquid, $\eta$, is a function of the shear rate, i.e., $$\eta = f(Y) \quad (9)$$

may either increase (shear thickening) or decrease (shear thinning) with increasing shear rates and can be characterized using a generalized Newtonian model. Generalized Newtonian models have the capability to describe the non-Newtonian viscosity without elucidating upon the time-dependent or elastic effects. One such empirical model that is widely used is the two-parameter power law expression:

$$\eta = m Y^{n-1} \quad (10)$$

where n (called the power law exponent) and m are constants characterizing the fluid. Representative values are n=1 for Newtonian fluids, n<1 for shear thinning and n>1 for shear thickening. The following relation between shear stress and shear rate for a power law fluid (Equation (11)) is obtained by using Equation (4):

$$\tau = \eta Y = m Y^n \quad (11)$$

where $\tau$ is the shear stress. For determination of non-Newtonian viscosity, the power law exponent, n may be determined by measuring $\tau$ and Y for a volume of fluid being sheared in a viscometer. A log-log plot of $\tau$ with Y yields a straight line and the power law exponent, n, is then derived from the slope of the straight line.

The working equations for shear stress and shear rate experienced by a moving liquid column inside a thin microfabricated rectangular capillary channel as used in the present embodiment are derived as follows. If one-dimensional flow inside a rectangular channel is (i.e., d<<w), the Cauchy equation that describes the shear stress is given by Equation 12:

$$0 = -\frac{\partial p}{\partial x} + \frac{\partial \tau_{yx}}{\partial y} \quad (12)$$

where $\tau_{yx}$ is the shear stress in the x direction (direction of flow) at constant y. The driving pressure gradient for the moving liquid column is directly proportional to the capillary pressure, $\Delta P$, and inversely proportional to the length of the liquid column, L:

$$\frac{\partial p}{\partial x} = \frac{\Delta P}{L} \quad (13)$$

If pressure gradient is independent of y, Equations (12) and (13) are solved to give the following expression for the shear stress at the wall:

$$\tau_w = \tau_{yx}\big|_{y=\frac{d}{2}} = \frac{\Delta P}{L} \cdot \frac{d}{2} \quad (14)$$

Moreover, if Equation (12) is solved using Equation (13) for a power-law fluid (Equation 11) and simplified, the shear rate at the walls inside a thin rectangular channel (d<<w) for the power law fluid is found to be:

$$Y_w = \frac{dv_x}{dy}\bigg|_{y=\frac{d}{2}} = \frac{6Q(t)}{wd^2}\left[\frac{2}{3} + \frac{1}{3n}\right] = \frac{6v(t)}{d}\left[\frac{2}{3} + \frac{1}{3n}\right] \quad (15)$$

where Q is the flow rate. Knowing $\tau_w$ and $Y_w$, the working equation for calculating the power law exponent, n may now be derived. After substituting Equations (14) and (15) in Equation (11), the following governing relationship for thin rectangular channels is obtained.

$$\frac{\Delta P}{L(t)} \cdot \frac{d}{2} = m \cdot \left(\frac{6v(t)}{d}\left[\frac{2}{3} + \frac{1}{3n}\right]\right)^n \quad (16)$$

Rearranging (16) provides Equation 17:

$$\frac{1}{L(t)} = \frac{2 \cdot m}{d \cdot \Delta P} \cdot \left(\frac{6}{d}\left[\frac{2}{3} + \frac{1}{3n}\right]\right)^n v(t)^n \quad (17)$$

where m, d, $\Delta P$, and n are constants for a given liquid sample and do not change with v(t) or L(t). By grouping all these constant terms together as a pre-factor, C, Equation 18 is obtained:

$$\frac{1}{L(t)} = C \cdot v(t)^n \quad (18)$$

L and v are measured on the microfabricated capillary viscometer and the power law exponent, n can be found from a log-log plot of 1/L vs. v. In the microfabricated capillary viscometer 1/L and v are essentially representative of the wall shear stress and wall shear rate respectively. Finally, the expression for the non-Newtonian viscosity is derived by combining (14) and (15), $$\eta = \frac{\tau_w}{Y_w} = \frac{d^2}{S} \frac{1}{\left(\frac{2}{3} + \frac{1}{3n}\right)} \frac{\Delta P}{vL} \quad (19)$$

The numerical constant in the denominator which otherwise comes out to be 12 is modified to "S" to allow for slight modifications in geometry, namely different ratios of width, w, and depth, d, which then empirically account for any "edge effects". For a Newtonian liquid, n=1 and Equation 19 reduces to Equation 1. Accordingly, non-Newtonian viscosity is determined by first measuring the power law exponent, n using Equation 18 and then computing vL, $d^2/S$ and $\Delta P$, as set forth above.

Figure 4:
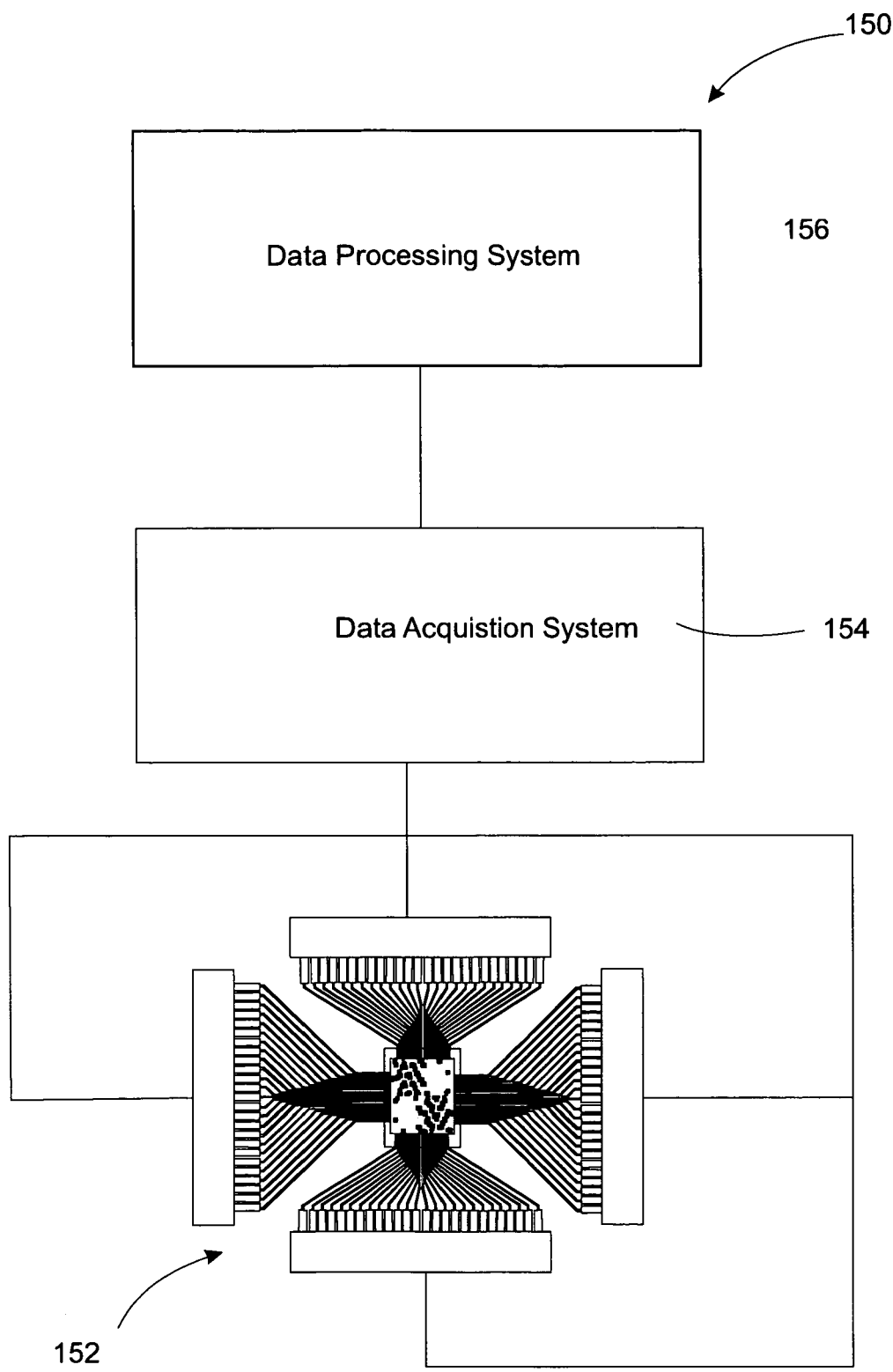
FIG. 4 is a schematic of an automated viscometer system.

In yet another embodiment of the invention, an automated nanoliter viscometer system that utilizes the viscometers set forth above is provided. With reference to FIG. 4, a schematic of the automated system is provided. Automated system 150 includes viscometer 152. Viscometer 152 includes the miniaturized channels described above. The flow rate meters and volume amount meters of viscometer 152 are in communication with data acquisition system 154. The data acquired by data acquisition system 154 is processed by data processing system 156. Data processing system 156 is typically a computer or microcomputer system. In one variation, the flow rate meters and volume amount meters are an electrode-based system. In particular, this electrode scheme is useful as an on-chip liquid detection is provided.

Figure 5:
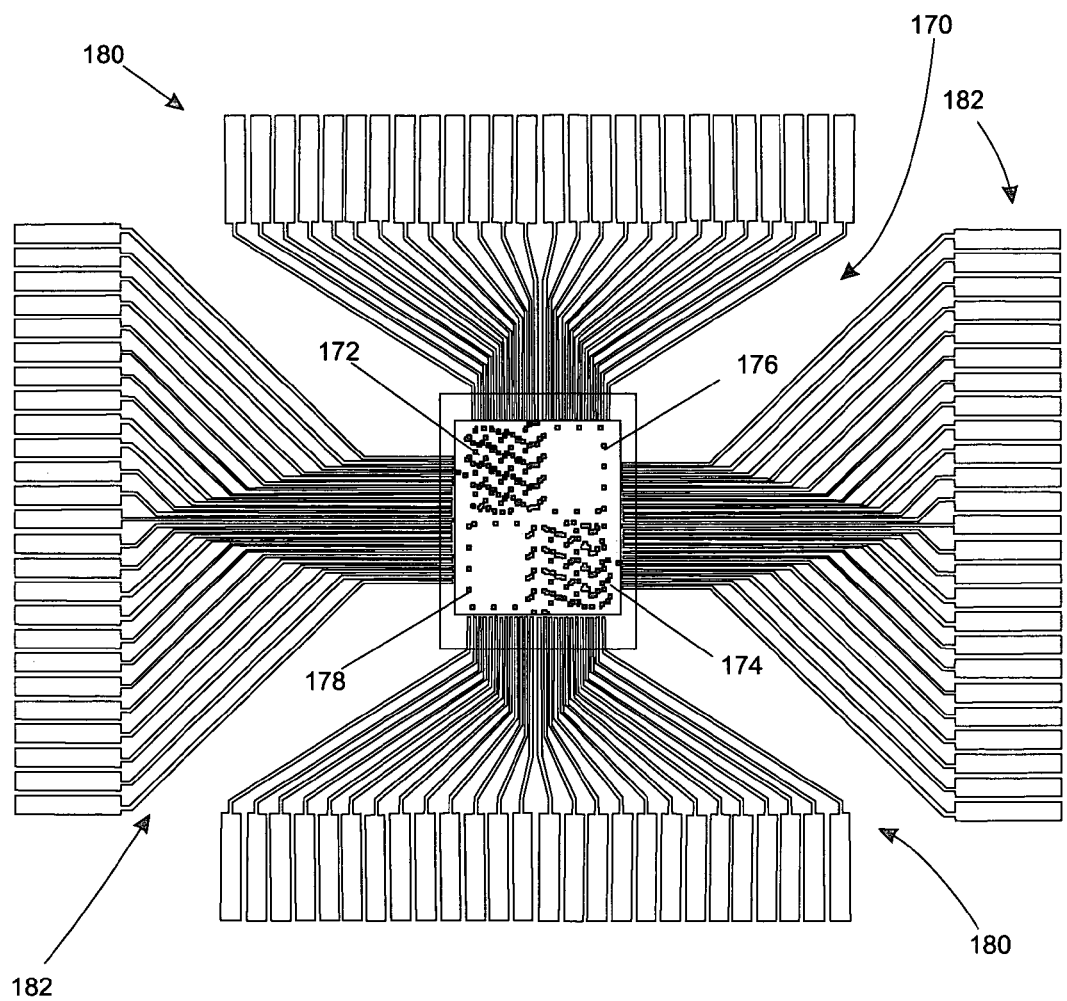
FIG. 5 is a top view of an electrode-based measuring system for measuring the rate of flow into the open channels of the invention and the amount of liquid in the closed end channels.
Figure 6A:
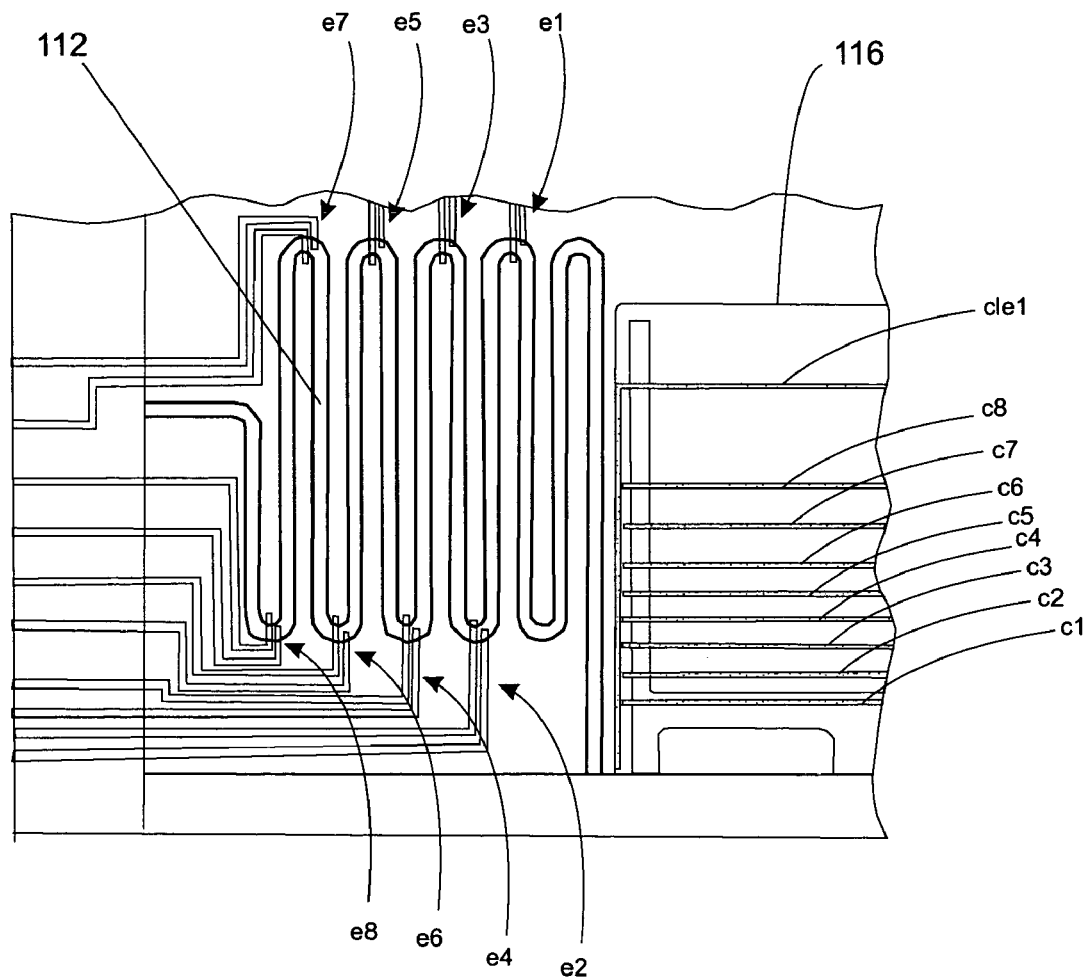
FIG. 6A is a top view of the placement of electrodes in the system of FIG. 5.
Figure 6B:
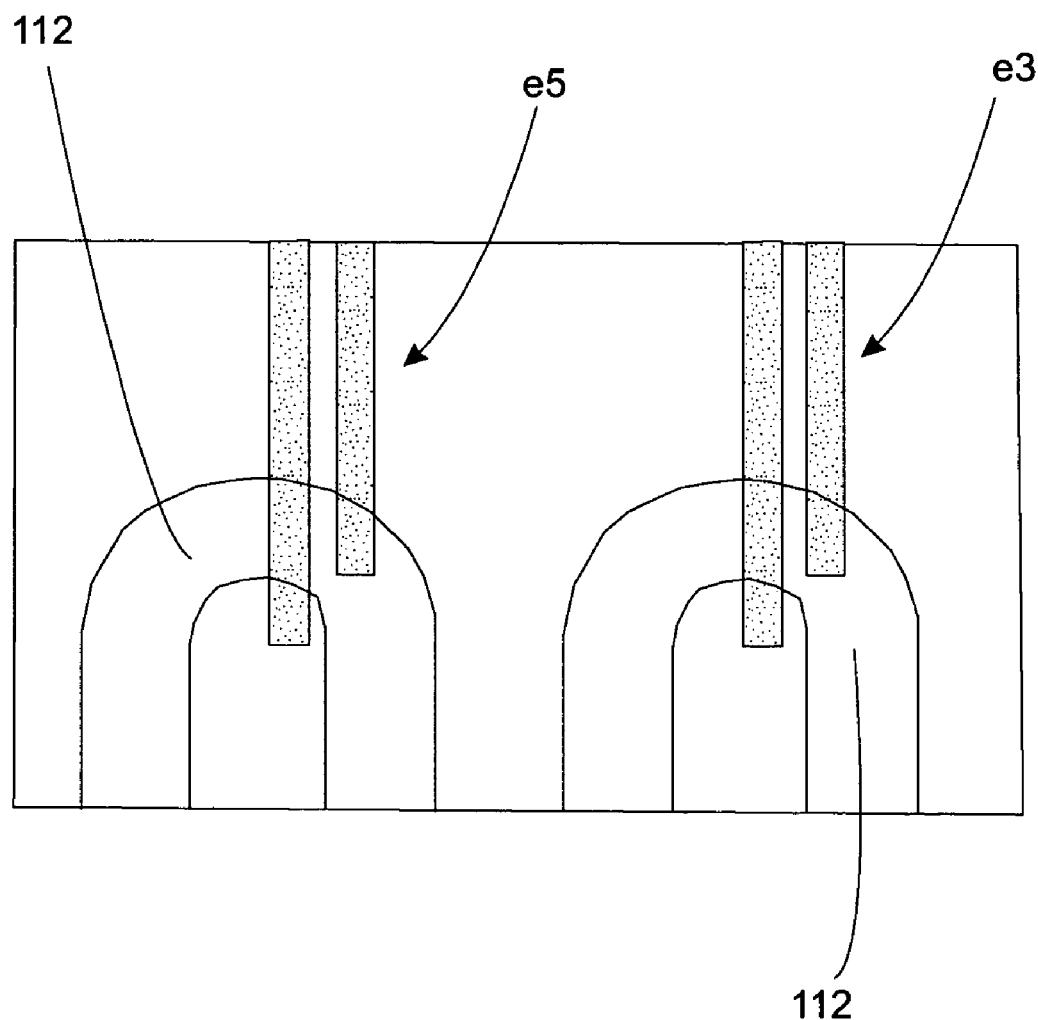
FIG. 6B is a magnified top view of the placement of electrodes in the system of FIG. 5.

With reference to FIGS. 5, 6A, and 6B, top views of an electrode liquid measuring system in communication with the viscometers of the invention are provided. Viscometer system 170 includes open channels 172, 174 and closed-end channels 176, 178. Electrode groups 180, 182 extend from within open channels 172, 174 and closed-end channels 176, 178. In a variation, a portion of electrode groups 180, 182 are deposited onto a channel defining surface. A voltage drop across the electrodes is used to detect the presence of a moving liquid droplet inside the channels 172, 174, 176, 178 at predetermined locations. The information on the location of the liquid droplet with time is then internally processed to give the liquid viscosity by data processing system 156. Electrode groups 180, 182 are formed from any suitably conductive material such as metals or conducting metal oxides and nitrides. Gold is particularly useful. Gold microelectrodes used for detection are fabricated using standard photolithographic techniques. The functioning of the device is completely controllable by a laptop computer and the total time for operation from setting up the device, on-chip calibration, adding the liquid sample and obtaining an electronically displayed viscosity value is about 4 minutes or less. All relevant calculations are performed by a computer control program in conjunction with the on-chip liquid detection system. With reference to FIGS. 6A and 6B, a portion of electrode groups 180, 182 are proximate to or within open channels 112, 114 and closed conduits 116, 118. For example, electrode pairs e1–e8 are proximate to the bends of open channels 112, 114 and electrodes c1e1 and c1–c8 are proximate to (or within) closed conduits 116, 118.

Figure 7:
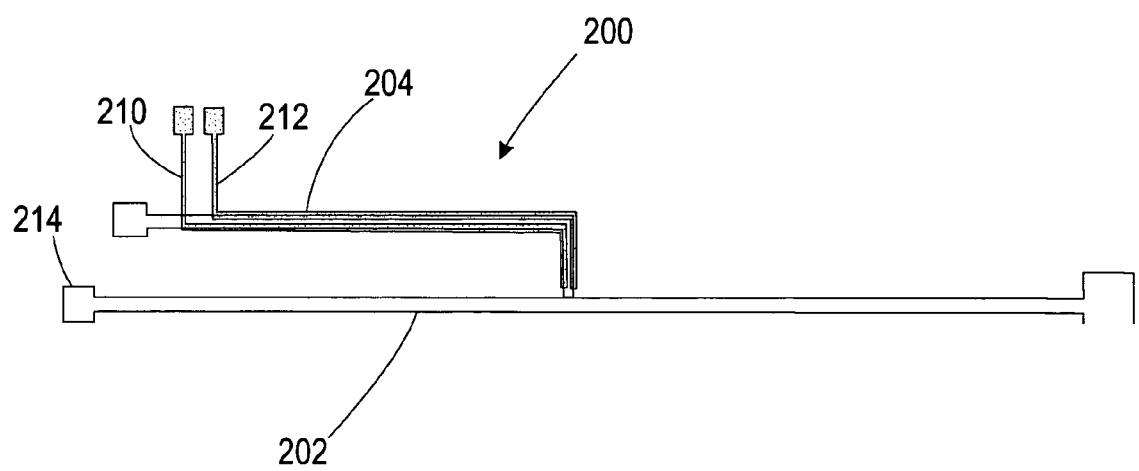
FIG. 7 is a schematic of an analog liquid measuring system.

In another embodiment of the invention, an "analog" method of measuring the volume (and hence, capillary pressure) of the liquid that has wicked into the sealed chamber is provided. FIG. 7 provides a schematic of a device utilizing the analog method of this embodiment. The electrode-based method of detecting liquid droplets as set forth above is "digital" in operation since a zero voltage indicates that no liquid is present while any non-zero voltage indicates that liquid is present over the electrodes. While such a "digital" method is appropriate for velocity inside the open channel ("OC"), the method may lead to slight errors in volume measurements inside the sealed chamber ("SC") if the equilibrium static meniscus of the liquid droplet falls between two electrodes. Accordingly, these errors are reduced by the analog detection technique of this embodiment in which the voltage response from the microelectrodes is a direct function of the volume of liquid over it.

With reference to FIG. 7, a schematic of the analog measuring device is provided. Microfluidic device 200 includes channel 202 and side channel 204. Parallel electrodes 210, 212 run along channel 204. A drop of liquid is added at inlet 214 and flows within channel 202. A portion of the liquid flows into channel 204. A voltage is applied across the electrodes and the steady state voltage response from the electrodes is recorded. The volume of liquid is carefully varied and similar voltage measurements are made for each volume. The plot of the steady state voltage response from the microelectrodes as a function of the droplet volume provides a calibration for device 200.

In still another embodiment of the invention, a thermal method of detecting the presence of nanoliter droplets inside a microfluidic channel is provided. In this embodiment, liquid droplets are detected through a combination of resistive heating and resistive temperature detection (RTD). The region where the liquid had to be detected is locally heated using an on-chip heater and the response of an adjacent temperature detector is monitored. As the liquid moves over the region, thermal mass of the liquid droplet carries heat away from the region and therefore lowers the local temperature. The local decrease in temperature is sensed by the on-chip RTD (resistive temperature detector).

The following examples illustrate the various embodiments of the present invention. Those skilled in the art will recognize many variations that are within the spirit of the present invention and scope of the claims.

I. Viscosity Measurements for Newtonian Fluids

A. Materials and Methods

Channel Fabrication

Glass wafers (Dow Corning Pyrex 7740, 500 µm thick, 100-mm diameter) are first annealed in an oven (Well Apparatus) at 550° C. Note that annealing at a temperature higher than 550° C. would cause the glass wafers to warp. After being annealed and piranha cleaned, a 500-Å-thick chrome layer followed by a 4000-Å-thick gold layer is deposited on the glass wafers. Photoresist (PR 1827, Hoest Celanese) is spun at 2000 rpm, patterned using a channel photomask, and developed in MF319 (Shipley Microposit). The metal layers are etched in commercial gold etchant (Gold Etchant TFA, Transene Co., Danvers, Mass.) and chrome etchant (CR-14, Cyantek Inc., Fremont, Calif.). The glass is then etched in a freshly prepared solution of hydrofluoric acid (30%). After the glass had been etched to the desired thickness (rate 6.8 µm/min), the photoresist is removed using PRS2000. Finally, the chrome and gold metal coatings are removed using their respective etchants and the wafer is diced on a dicing saw to yield individual glass dies. The depth and width of the channel on each device are analyzed on a surface profiler (Alpha-Step 500, KLA-Tencor).

Device Bonding

The glass die is bonded to the silicon substrate (0.2-µm-thick layer of thermal oxide is grown on silicon) using an optical adhesive (SK-9, 40 cP, Summers Optical, Fort Washington, Pa.). A miniscule amount of the adhesive is applied to the corners of the device using a paintbrush. The adhesive is drawn into the gap between silicon and glass by capillary action and stops at the edge of the channels. After repeated applications, it is cured under an ultraviolet light source (365 nm) for 1 hour.

Experimental Setup for On-Chip Viscosity Measurement

The experiments on the microfabricated viscometer are conducted on an Olympus SZX12 stereomicroscope. For measuring viscosity of blood plasma, the device is kept on a hot plate. The hot plate is maintained at a temperature (38.5° C.) so that the temperature on the surface of the device is steady at 37° C. The blood plasma sample is also preheated to 37° C. before adding to the device. The liquid is added to the device using a precision microliter pipet (Rainin Instrument, LLC, Oakland, Calif.). A 5-µL volume of liquid is added for each experimental run, unless otherwise stated. For the self-calibrating nanoliter viscometer, only one drop of liquid is added to the device, a part of the drop wicked into the sealed channel while the other part traveled inside the open channel. Deionized water is used for all viscosity experiments. The experiments are recorded on a videocassette through a Nikon Coolpix 4500 camera and then transferred to a computer using Adobe Premiere 6.5 Pro Software. The movies are analyzed in Adobe Premiere and data on length of the liquid as a function of time is extracted.

Contact Angle Measurements

The device (oxidized silicon or glass) over which the contact angle is to be measured is placed on a horizontally leveled x-y stage of the probe station. A color CCD camera (Topica, TP-6001A) mounted on a tripod is set up to take a side picture of the device and is aligned to be level with the x-y stage. A 2-µL drop of the liquid is then placed on the device and a side photograph of the drop profile is taken using the CCD camera. The contact angle is then deduced from the photograph by drawing a line against the curvature of the drop at the point of contact with the surface.

Off-Chip Viscosity Measurements

The macroscale/off-chip viscosity measurements are performed on the AR1000 rheometer (TA instruments rheology division ST-B). The device had cone and plate geometry; a 2° cone and 6-cm plate is used. At least 2 mL of test sample is required in order to measure viscosity of this rheometer. Note that this volume of the sample is at least 3 orders of magnitude more than what is required on the microfabricated viscometer.

Preparation of the Plasma Sample

Whole blood is collected from patients and centrifuged at 3800 rpm for 6 min. Plasma, which comprises the supernatant liquid, is aliquoted out.

Accuracy and Precision of Results

The results from the microfabricated viscometer are reported as the MV (SD, where MV is mean value and SD is the standard deviation. The accuracy is defined as the relative deviation of the measured MV from the literature value or the value calculated on a commercial viscometer. Precision is defined as the SD normalized by the MV.

B. Results

Simple Viscosity Measurements

A microfabricated capillary viscometer is constructed as shown in FIG. 1. The viscometer contains a single channel 20 with depth ("d") of about 5 µm, a width of about 340 µm, a total length ("Ltotal") of about 10 cm, and S=12 (approximate slit geometry)). As set forth above, channel 20 is open on both ends to allow liquid to enter from one end and displace air to exit from the other. The microfabricated viscometer required no external actuation for operation and, unlike most commercial viscometers, does not contain any moving parts. Capillary pressure not only draws the liquid sample inside the microfabricated viscometer but also provides the driving force for the liquid to move forward inside the channel. The mean velocity of the liquid as it moves along the microfluidic channel by this force is used to calculate the viscosity of the liquid.

Figure 8A:
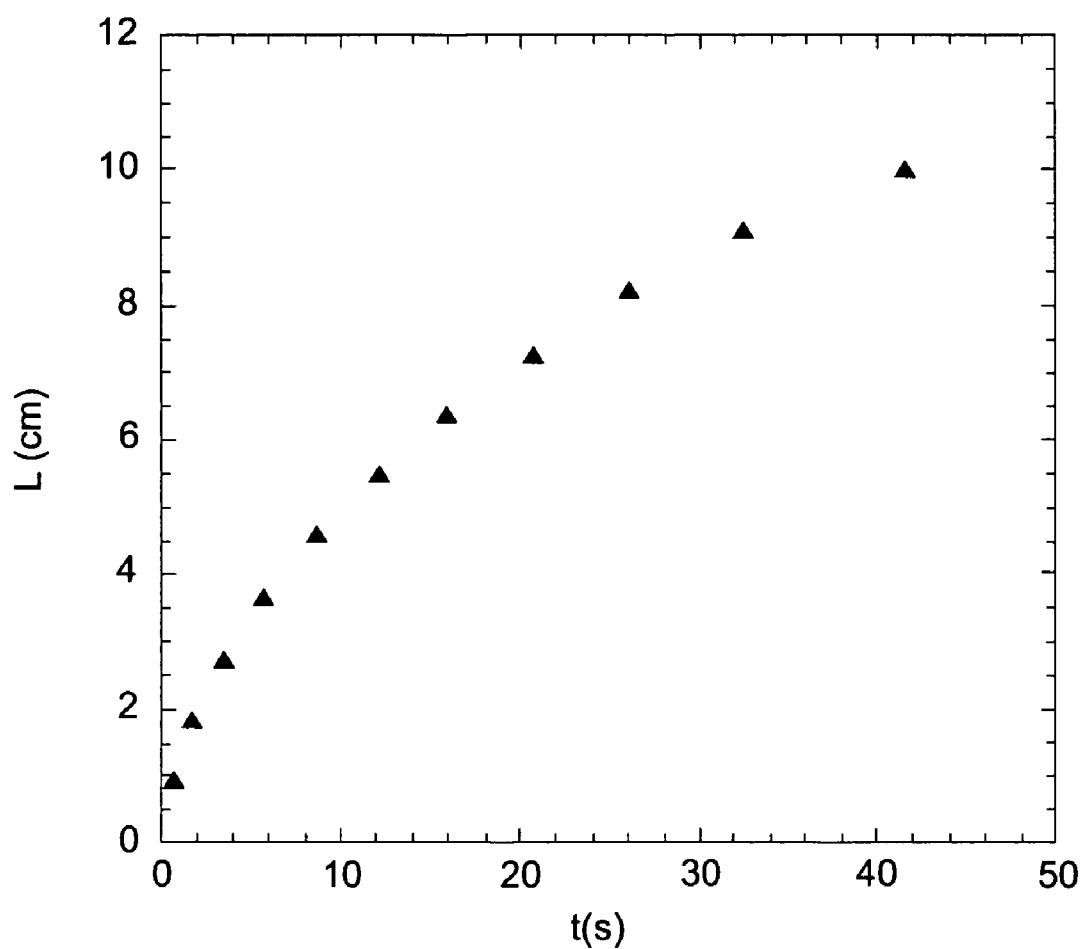
FIG. 8A is a plot of the length of the liquid column, L inside the channel as a function of time (L is defined as the distance of the advancing liquid front from the inlet measured in the channel)
Figure 8B:
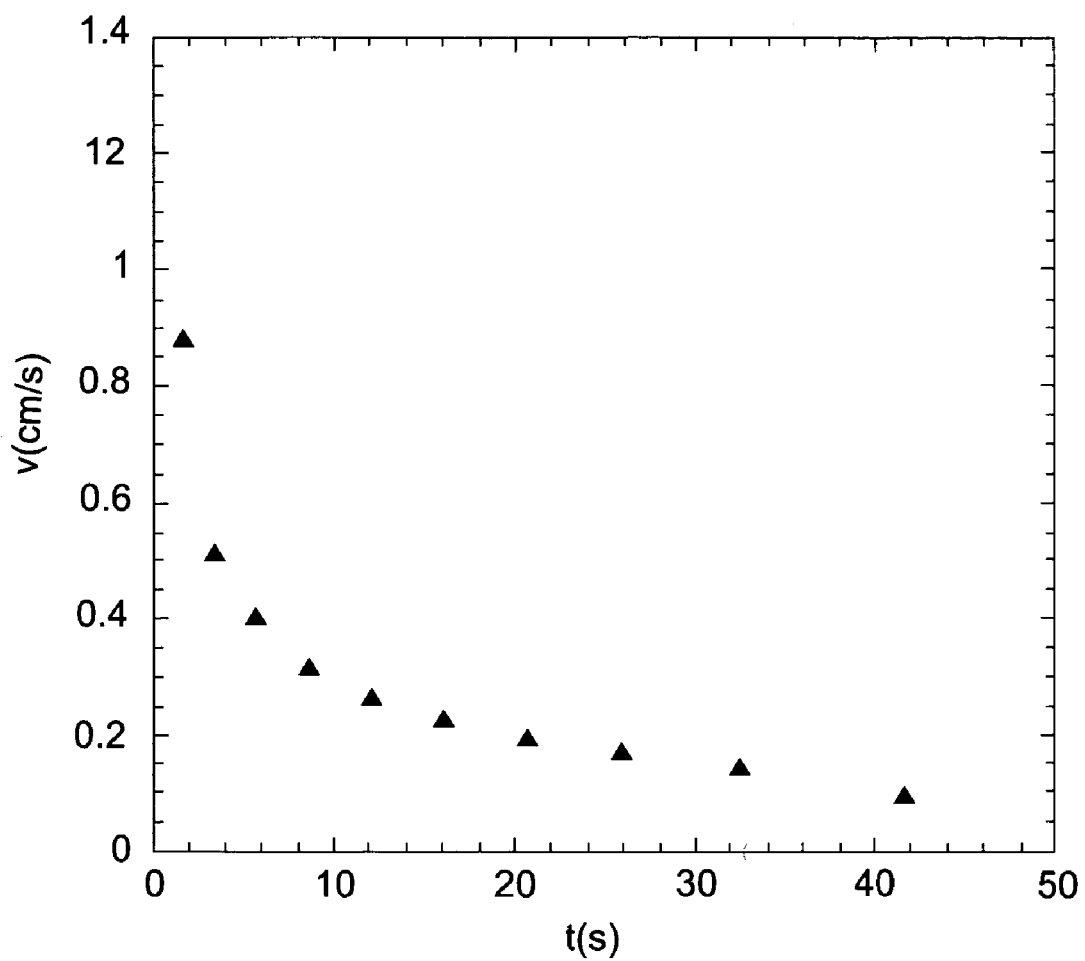
FIG. 8B is a plot of the the mean velocity of the imbibing liquid column as a function of time calculated using the incremental increase in the liquid column over short times (i.e., $v=\Delta L/\Delta t$)
Figure 8C:
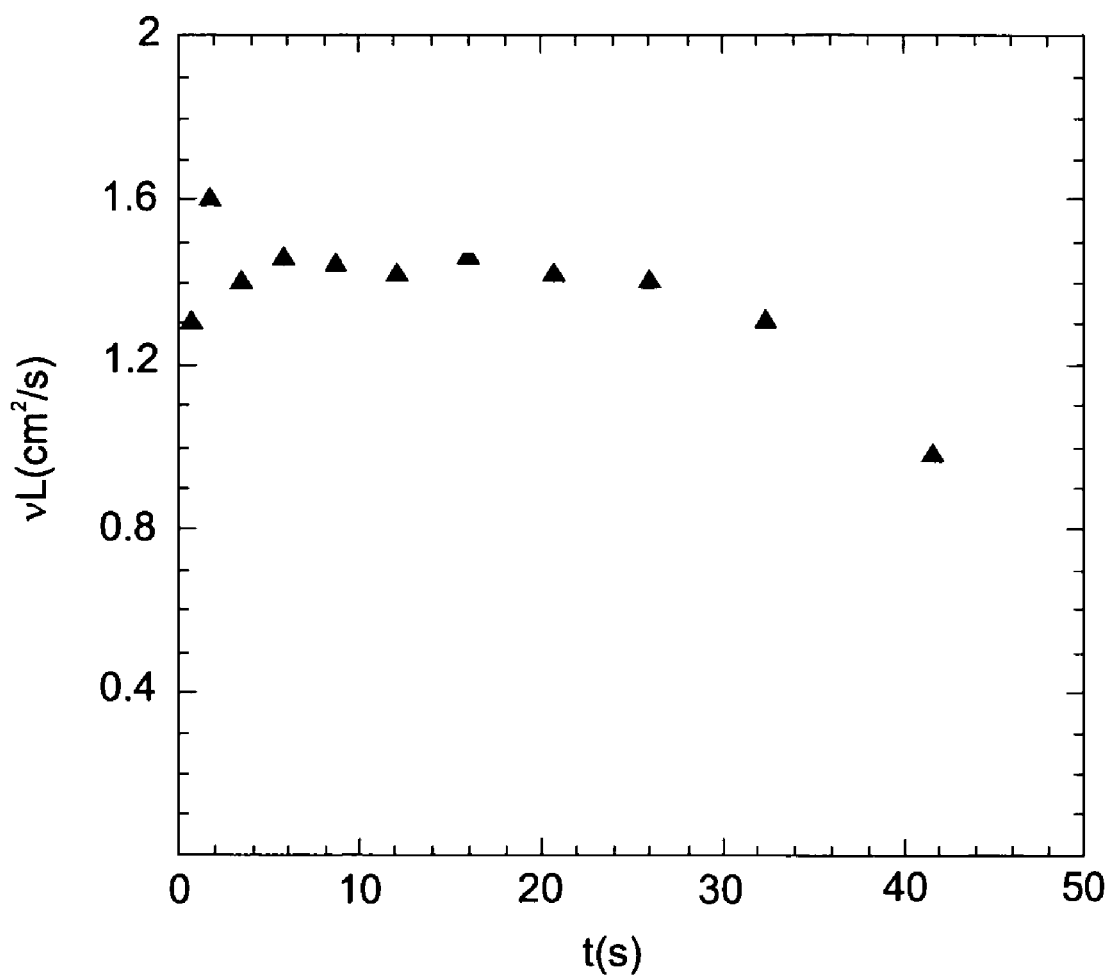
FIG. 8C is a plot of the calculated vL is using the data from the data of FIGS. 8A and 8B.

Viscosity is determined by measuring the product of the velocity and the liquid column length, which is then used in Equation 2. A 5-µL drop of solution (e.g., water) is placed at the inlet of the channel and is spontaneously drawn into the hydrophilic channel by capillary pressure. Contributions due to gravity are neglected since the device is used on a horizontal surface and no external air pressure or vacuum needs to be applied. While the liquid is in motion, the length of the liquid column inside the channel, L, which is defined as the distance along the channel between the advancing front of the liquid inside the channel and the inlet of the channel, is monitored as a function of time (FIG. 8A). The incremental increase in the length ($\Delta L$) over short times ($\Delta t$) is used to calculate the velocity of the imbibing liquid column (i.e., v) $\Delta L/\Delta t$, FIG. 8B). The product of velocity and length (i.e., vL) is relatively constant to within (7% throughout the channel, deviating mainly at the entrance and the exit (FIG. 8C). A simple mean of the intermediate constant values of vL (1.43 cm2/s, in this case) is computed and used to calculate the viscosity.

Without limiting the present invention to any particular theory of operation, observed deviations in the product vL could be due to a number of factors. The deviations in the beginning are primarily due to sudden contraction at the entrance, experimental error in measuring $\Delta L$ ($v=\Delta L/\Delta t$), or because the flow has not yet developed fully into Poiseulle flow. Near the exit, the advancing liquid front starts to creep along the hydrophilic channel walls and thus deforms the advancing meniscus. Such a deformed meniscus has a nonuniform radius of curvature ($R_2$), which leads to the deviations in the mean velocity of the liquid. Despite these deviations at the beginning and at the end, the intermediate values are relatively constant (FIG. 8C) and are used to calculate the viscosity of the liquid.

Having found vL and knowing $d^2/S$, the capillary pressure, $P_{capillary}$, is still needed to calculate the viscosity using equation 2. The surface tension of water is 72.6 dyn/cm at 22° C. and the contact angle, on both glass and oxidized silicon, is measured to be 30°, yielding a capillary pressure ($P_{capillary}$) for water in the device of 991 N/m² (eq 5). The viscosity was then calculated from eq 2. An average of the 25 runs resulted in a viscosity value of 0.987 (0.225 cP at 22° C. The measured viscosity of water compares favorably (within 1%) with both the literature value of 0.981 cP and the measurements on a commercial cone and plate viscometer (AR1000 rheometer), which gave a value of 1.005 cP at 22° C.

Self-calibrating Viscometer Measurements

The self-calibrating viscometer is first tested with a viscosity standard (Paragon Scientific Ltd., UK, Medical standard D2.0). Using water as the calibration liquid, $vL_{calib}$ is measured from an open channel 86 of FIG. 3A (also referred to as "$OC_1$"). The procedure for measuring $vL_{calib}$ is the same as the one used for liquids in the simple viscosity measurements. $P_{capillary,calib}$ is calculated from sealed chamber 82 of FIG. 3A (also referred to as "$SC_1$") using equation 5. After the addition of the viscosity standard sample, the capillary pressure for the sample, $P_{capillary,sample}$, was calculated using sealed channel 84 of FIG. 3A (also referred to as "$SC_2$") and $vL_{sample}$ measured from the $OC_2$. By using eq 8, the viscosity of the sample was calculated to be 2.045 (0.190 cP at 23° C., which compares well with the manufacturer's value of 2.121 cP. Thus, the use of additional calibrating channels that measure $d^2/S$ and $P_{capillary}$ led to improved precision of viscosity measurements (9 vs 23%), and prior information about the liquid sample or the device was not required.

The self-calibrating nanoliter viscometer is used to test the viscosity of blood plasma collected from patients. Blood plasma viscosity is useful in evaluating patients with elevated serum immunoglobulins, multiple myeloma, mucosal bleeding, blurred vision, or neurologic symptoms suggesting a hyperviscosity syndrome. Symptoms of hyperviscosity are commonly seen when the plasma viscosity exceeds 4 cP. Patients with elevated values (>4 cP; normal range 1.20–1.85 cP) are candidates for apheresis. For measurements at 37° C., the calibration liquid and the sample are preheated to 37° C., and the nanoviscometer was maintained at 37° C. by placing it on a hot plate during the course of the experiment. Note that metal heaters can be built into the device to allow for integrated measurements at elevated temperatures, eliminating the need for external heating. The nanoliter viscometer gave a viscosity value of 1.433 (0.180 cP at 37° C., which compares favorably with the value of 1.413 cP measured on a cone and plate viscometer (Brookfield LV DV-I).

Design and Operational Considerations

Devices with alternate geometries have also been analyzed. To check the hypothesis that the square turns of the serpentine channel might be leading to deviations from plain Poiseuille flow and thus introducing error in the viscosity measurements, channels with round turns are fabricated. The flow of liquid at the round turns was smoother when compared to square turns; in square turns, bubbles would occasionally get trapped at the corners. Also note that for better utilization of space the sealed channel was replaced by a square chamber. In a square chamber, one can get a higher etched volume using the same area/footprint of the device by essentially eliminating the wall area between the segments of the serpentine channels. Consequently in order to achieve a certain volume $V_1$, a square chamber would use less space/footprint as compared to a channel. A plasma sample tested on the round turn viscometer gave a viscosity of 1.456 (0.163 cP at 37° C. (precision 11%). When compared to the results from devices with square turns, the precision was almost identical, indicating that either channel geometry is acceptable.

In other tests, the effect of the technique of adding the liquid at the inlet of the channel is investigated for two different cases. In either case, a 5-µL volume of the liquid was added using a pipet tip. In the first method, referred to as top loading, the liquid drop is placed directly on top of the channel at the entrance and is immediately wicked inside the channel. In the second method, referred to as side loading, the liquid drop is added on the silicon surface slightly away (2 mm) from the channel inlet, and as it spreads on the surface, it encounters the glass channel inlet and is then drawn into the channel. The initial velocity inside the channel was found to be a weak function of the loading, but the velocities for different loadings quickly converged to the same profile as the liquid moved inside. Although the difference is essentially irrelevant, the method of drop loading is maintained consistent between the calibration and test liquids.

II. Viscosity Measurements for Non-Newtonian Fluids

A. Materials and Methods

Glass and Silicon Fabrication

The silicon glass hybrid device is manufactured using standard photolithographic procedures and is detailed elsewhere 13. Briefly, a borofloat glass wafer (Dow Corning Pyrex 7740) is annealed at 570° C., piranha cleaned and coated with a masking metal layer (500 Å Cr/4000 Å Au). The glass wafers are then patterned and the exposed metal layer is removed using a gold etchant (Gold Etchant TFA, Transene Co., Danvers, Mass.) and a chrome etchant (CR-14, Cyantek Inc., Fremont, Calif.) and then etched in 49% HF (rate~6.8 µm/min). The depth and width of the channel on each device are analyzed on a surface profiler (Alpha-Step 500, KLA-Tencor).

Glass and Silicon Assembly

The glass and silicon wafers are diced separately. The glass side is then bonded to the silicon side using an optical glue (SK-9, 40 cp, Summers Optical, Fort Washington, Pa.) and cured under UV light for 4–5 hours.

Experimental Set-up for On-Chip Viscosity Measurement

The experiments are performed on the device oriented horizontally on an x-y stage of an Olympus SZX12 stereomicroscope. A precision microliter pipette (Rainin Instrument, LLC, Oakland, Calif.) is used to add liquid sample (~5 µL) to the device. The experiments are recorded on a videocassette through a Nikon Coolpix 4500 camera with a capture rate of 30 frames/s and then transferred to the computer using iMovie.

Off-Chip Viscosity Measurements

The macroscale control viscosity measurements are performed on the AR 1000 rheometer (TA Instruments) using a cone and plate geometry. A 2° cone and 6 cm plate is used. All measurements are performed at 23° C.

Preparation of Polymeric Solutions

Four polymeric solutions are prepared for analysis. These are (a) 500 ppm WSR301 (Polyethylene oxide (PEO), MW~4M, Dow Chemical, Midland, Mich.), (b) 2000 ppm WSR308 (Polyethylene oxide (PEO), MW~8M, Dow Chemical, Midland, Mich.) (c) 2000 ppm A 110—(Hydrolyzed Polyacrylamide (PAM), 18%, MW~7–8 M, Cytec Industries Inc., West Patterson, N.J.) (d) 1000 ppm of Xanthan Gum (Sigma-Aldrich, St Louis, Mo.). 1000 ppm solution of Xanthan Gum, dilute solution of PEO (WSR 301) at 500 ppm and semi-dilute solutions of PEO (WSR 308) and PAM (A1100) at 2000 ppm are prepared in deionized (DI) water. To prevent shear degradation, polymer dissolution is performed in 500 mL bottles rotated at 3 rpm (Wheaton Science Products, Millville, N.J.). Dissolution required 2–3 days by this method. To minimize the effect of other mechanisms of degradation, experiments are performed within 1–2 days after the stock solution is prepared.

Whole Blood Sample Preparation

The blood samples are procured from Lampire Biological Laboratories (Pipersville, Pa.). The bovine blood samples are coagulated with 3% Na-EDTA and stored at 4° C. The blood samples are allowed to reach room temperature before testing and are thoroughly mixed to ensure a homogenous sample is loaded to the device. Each microfabricated device is used only once.

B. Results

Equipment Considerations

A self-calibrating microfabricated capillary viscometer that contains two open channels and two sealed chambers is shown in FIG. 3A. While the viscometer is initially developed for testing only Newtonian liquids, we now present a simple extension of its operation to include non-Newtonian liquids. Equation 19 will be the working equation that will be used to derive the non-Newtonian viscosity as a function of shear rate. The unique and enabling feature of the microfabricated viscometer is that the mean velocity of the liquid column, v does not remain constant with time but instead changes continuously as the liquid moves from the inlet to the outlet. Due to the variation in the mean velocity of the moving liquid column, a range of shear rates can be obtained during a single experimental run, which enables the viscometer to analyze non-Newtonian liquids.

Variation of Wall Shear Rates in a Single Experimental Run

Figure 9:
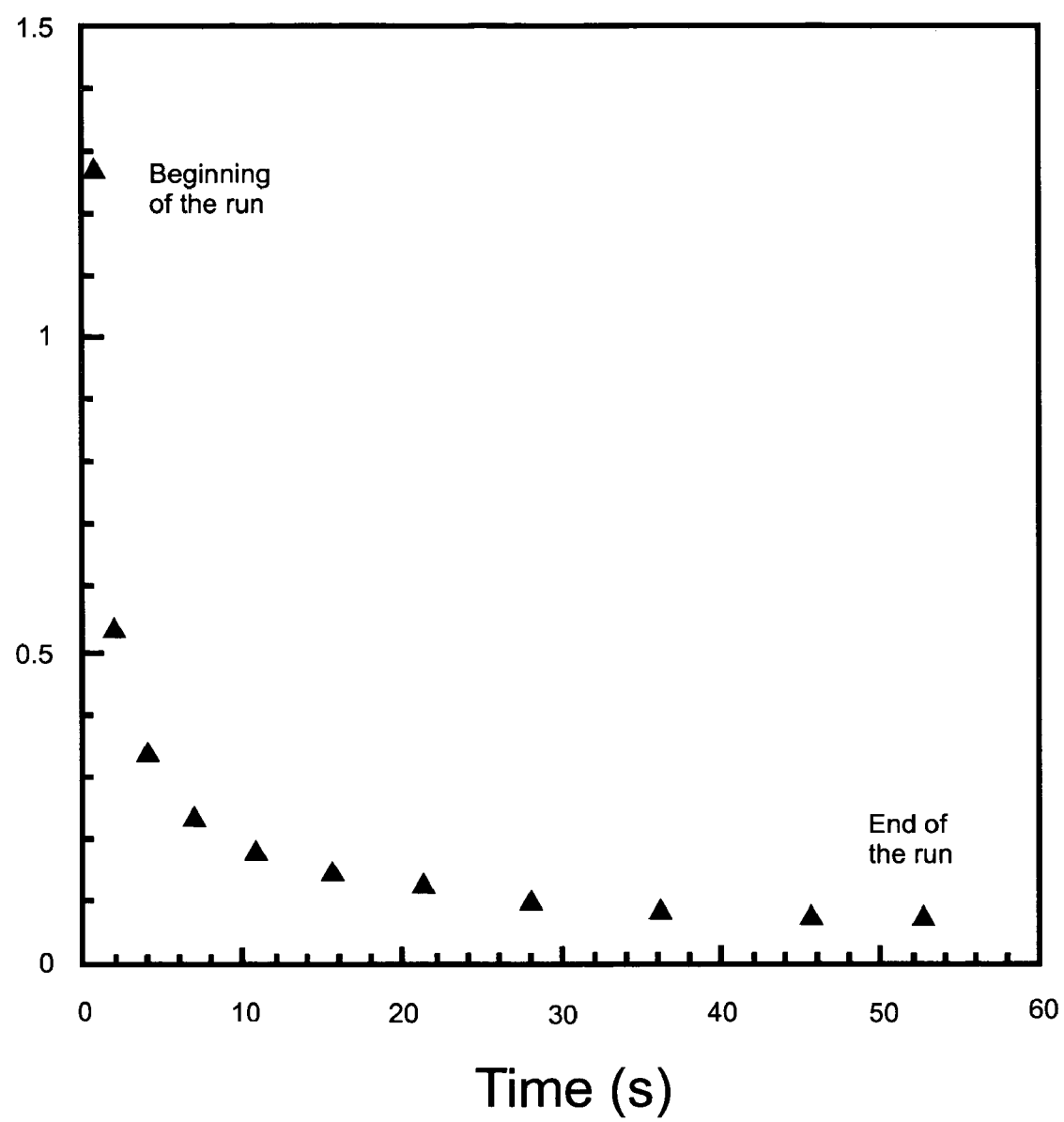
FIG. 9 is a plot of the mean velocity, v of the imbibing column of whole bovine blood inside the open channel of a viscometer as a function of time, t.

To ensure that a range of shear rates is obtained in the open channel of the viscometer, the first step is to measure the mean velocity of the liquid column, v inside the open channel. For this, a 5 µL drop of the liquid sample; whole bovine blood in this case, is placed at the inlet of the channel and is spontaneously drawn inside the channel by capillary pressure. It is observed that part of the liquid drop moves into the sealed chamber (SC) from where the driving capillary pressure is calculated (described later). While the liquid is in motion, the length of the liquid column inside the channel, L, which is defined as the distance between the advancing meniscus of the liquid inside the open channel and the inlet, is monitored as a function of time, t. The incremental increase in the length ($\Delta L$) over short times ($\Delta t$) is used to calculate the mean velocity, v as $\Delta L/\Delta t$ (FIG. 9). From the plot in FIG. 9 it may be extracted that the wall shear rate, which is proportional to the mean velocity (from Equation 15) will also vary in the same fashion. An order of magnitude change in the wall shear rate is evident from the beginning to the end of the run indicating that a non-Newtonian liquid can be analyzed with the viscometers of the present invention. Note that higher shear rates are obtained at the inlet of the channel (corresponding to the beginning of the experimental run) while lower shear rates are obtained towards the outlet of the channel (corresponds to the end of the experimental run).

Measurement of Power Law Exponent, n

Figure 10:
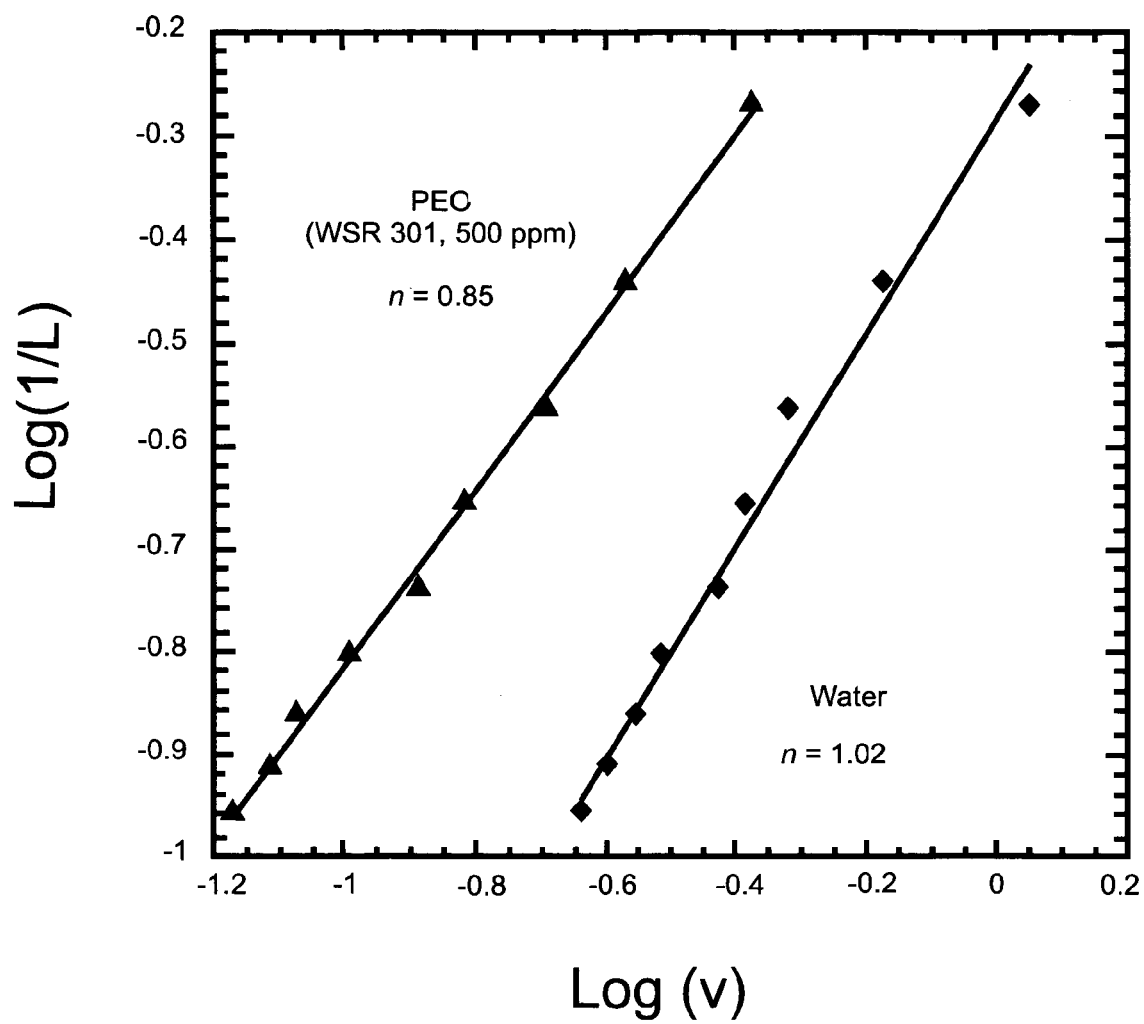
FIG. 10 is a log-log plot of 1/L with v for a dilute solution of Polyethylene Oxide (PEO, 500 ppm)

The first step in analyzing non-Newtonian liquid samples is determining the power law exponent, n. For this, 1/L and v are plotted on a log-log plot. The resulting plot is a straight line and n is found from the slope of the straight line in accordance with equation (12). The procedure for measuring n is first tested with a dilute solution of Polyethylene oxide (PEO; 500 ppm). A series of experimental runs are performed using PEO, each on a new microfabricated viscometer device. The mean of the n values is found to be 0.85+0.03 at 23° C. (precision 3.5%). FIG. 10 shows the log-log plot of 1/L vs. v for a specific run for which n equals 0.85; as a control, the power law exponent for water, which is a Newtonian fluid is also computed on the microfabricated viscometer and is found to be 1.02. For further validation, the measurement of n from a traditional cone and plate viscometer is performed. For the cone and plate viscometer, the experimentally measured shear stress and shear rate are plotted on a log-log plot and the slope of the straight line gives n. The power law exponent n for the dilute solution of PEO is found to be 0.88 from the cone and plate viscometer, which compared well with the microfabricated viscometer to within 3%.

Measurement of vL, $\Delta P$ and $d^2/S$

The next step in determining the non-Newtonian viscosity using Equation (13) is the measurement of vL, $\Delta P$ and $d^2/S$ which has been described previously. Briefly, vL is calculated from the data on v and L. $\Delta P$ is found from the sealed chamber (SC); a drop of liquid placed at the only inlet of the chamber is spontaneously drawn into the chamber. The trapped air is compressed as the liquid moves in to balance the capillary pressure difference; the air pressure inside the channel after the drop moves in exceeds the atmospheric pressure by an amount equal to the capillary pressure. Using the ideal gas law, we obtain:

$$d^2/S = \mu_{calib}(vL_{calib}/P_{capillary,calib}) \quad (7)$$

where $V_1$ is the original volume of air inside the sealed chamber and $V_2$ is the volume of the compressed air found from the position of the air/liquid meniscus. Finally, $d^2/S$ is measured by using a calibration liquid (Newtonian) of known viscosity, $\mu_{calib}$ (e.g., water) on an open channel (i.e., $OC_1$) and sealed chamber (i.e., $SC_1$). Measuring $vL_{calib}$ from $OC_1$ and Pcapillary,calib from $SC_1$, $d^2/S$ is found from using Equation (1):

$$P_{capillary} = P_{atm}(V_1/V_2 - 1) \quad (6)$$

Since both open channels ($OC_1$ and $OC_2$) on the device are of identical geometry, the calculated value of d2/S from $OC_1$ applies for the second open channel $OC_2$.

Non-Newtonian Viscosity Profile of Whole Bovine Blood

Using the above described methods for measuring n, vL, $d^2/S$ and $\Delta P$ and then employing Equation 19 the non-Newtonian viscosity of whole bovine blood is measured as a function of shear rate. First, n is extracted from the slope of the log-log plot of 1/L with v and found to be 0.78 which compares well with that measured on the cone and plate viscometer (0.75) and also with the n values in literature (~0.80). Second, vL is measured; it may be noted that the term vL in Equation 19 is no longer a constant as it used to be for a Newtonian liquid, but instead varies as the liquid moves into the channel. Third, $d^2/S$ is found from (15) to be 17.28×10$^{-10}$ m$^2$/s using water as a calibration liquid. Finally, ΔP was calculated from the sealed chamber using Equation 6 to be 996 Pa.

Figure 11:
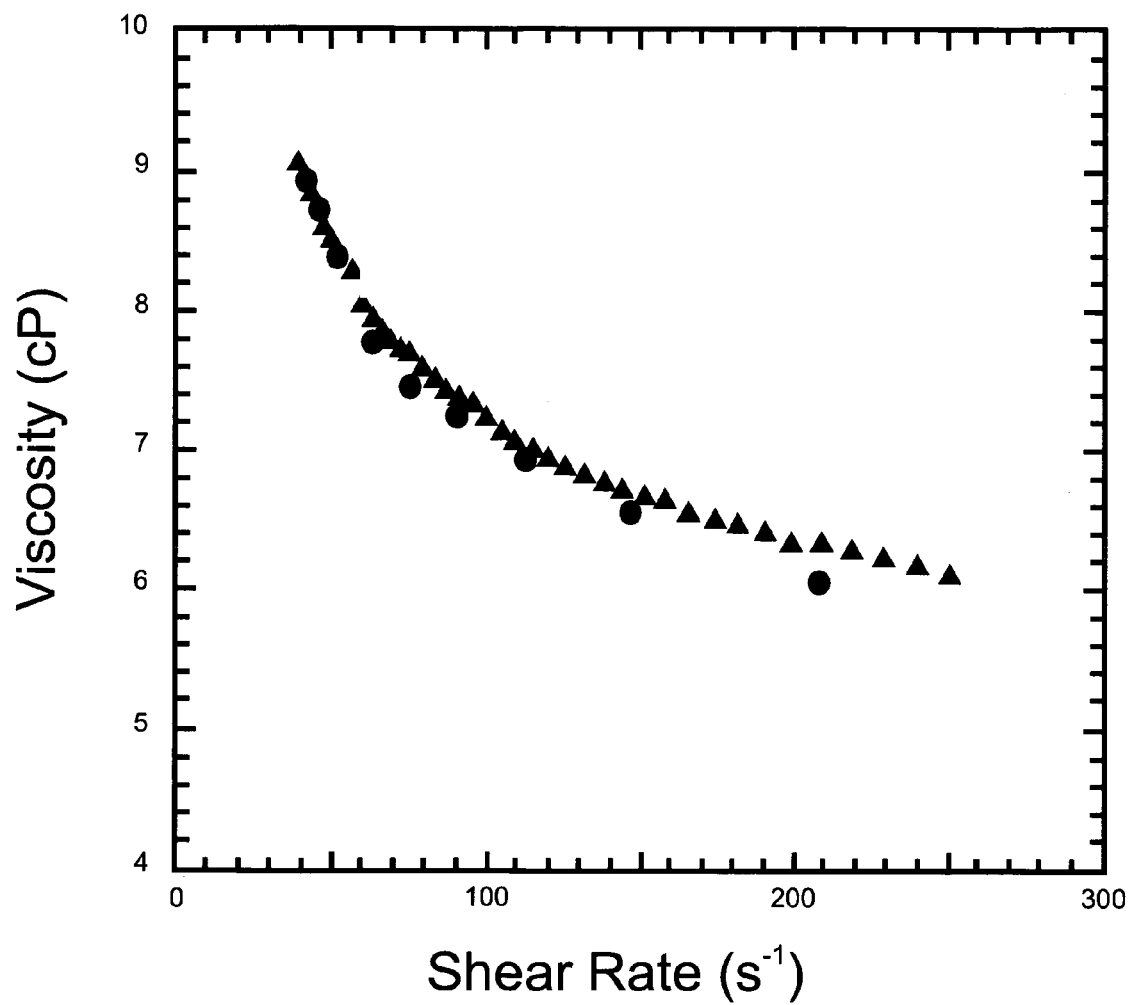
FIG. 11 is a plot of the viscosity (at 23° C.) of whole bovine blood as a function of shear rate is plotted (filled circles); for comparison, the corresponding results from the cone and plate viscometer (AR 1000, TA Instruments) are also shown (filled triangles)

Knowing n, vL, d$^2$/S and ΔP, the non-Newtonian viscosity profile is calculated from Equation 19 at 23° C. and is shown as function of shear rate in FIG. 11. The wall shear rate is calculated knowing n, v and d (100 μm) and using Equation 15; the shear rate for this particular experimental run varied from 20–200 s$^{-1}$. Agan, viscosity measurements from the cone and plate viscometer are used for validation and show good agreement.

Non-Newtonian Viscosity of Dilute and Semi-Dilute Solution of Linear Flexible Polymer Molecules (PEO and PAM) and Viscous Stiff Polymer Molecule (Xanthan Gum)

Other polymeric solutions that are known to exhibit shear thinning viscous and viscoelastic behavior are also analyzed on several microfabricated capillary viscometers. These additional studies are conducted to test the robustness of the viscometer and its capability in testing a variety of polymeric solutions. To validate the functioning of the microfabricated viscometer with a highly viscous shear thinning behavior of a stiff polymer chain, an aqueous solution of Xanthan Gum is selected. For validation with linear flexible polymers molecules, solutions that are routinely analyzed such as Polyethylene oxide and Polyacrylamide are selected. Since the viscosity and elasticity of these polymers varies with the concentration, both dilute as well as semi-dilute regimes are investigated.

Figure 12:
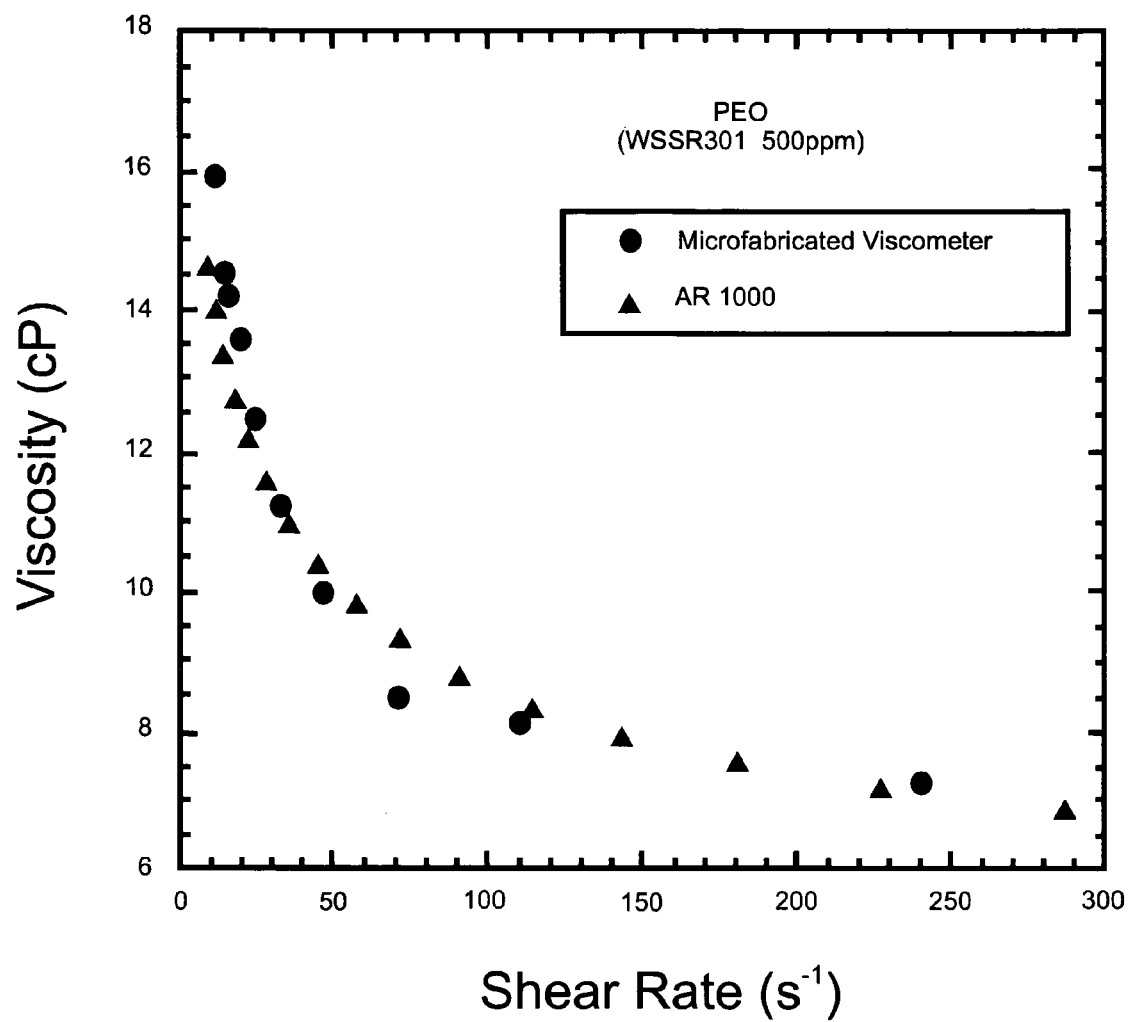
FIG. 12 is a plot of non-Newtonian Viscosity (cP) as a function of Shear Rate (s–1) for a dilute solution of Polyethylene Oxide (PEO, WSR301, 500 ppm) at 23° C.; for comparison, the corresponding results from the cone and plate viscometer (AR 1000, TA Instruments) are also shown (filled triangles)
Figure 13:
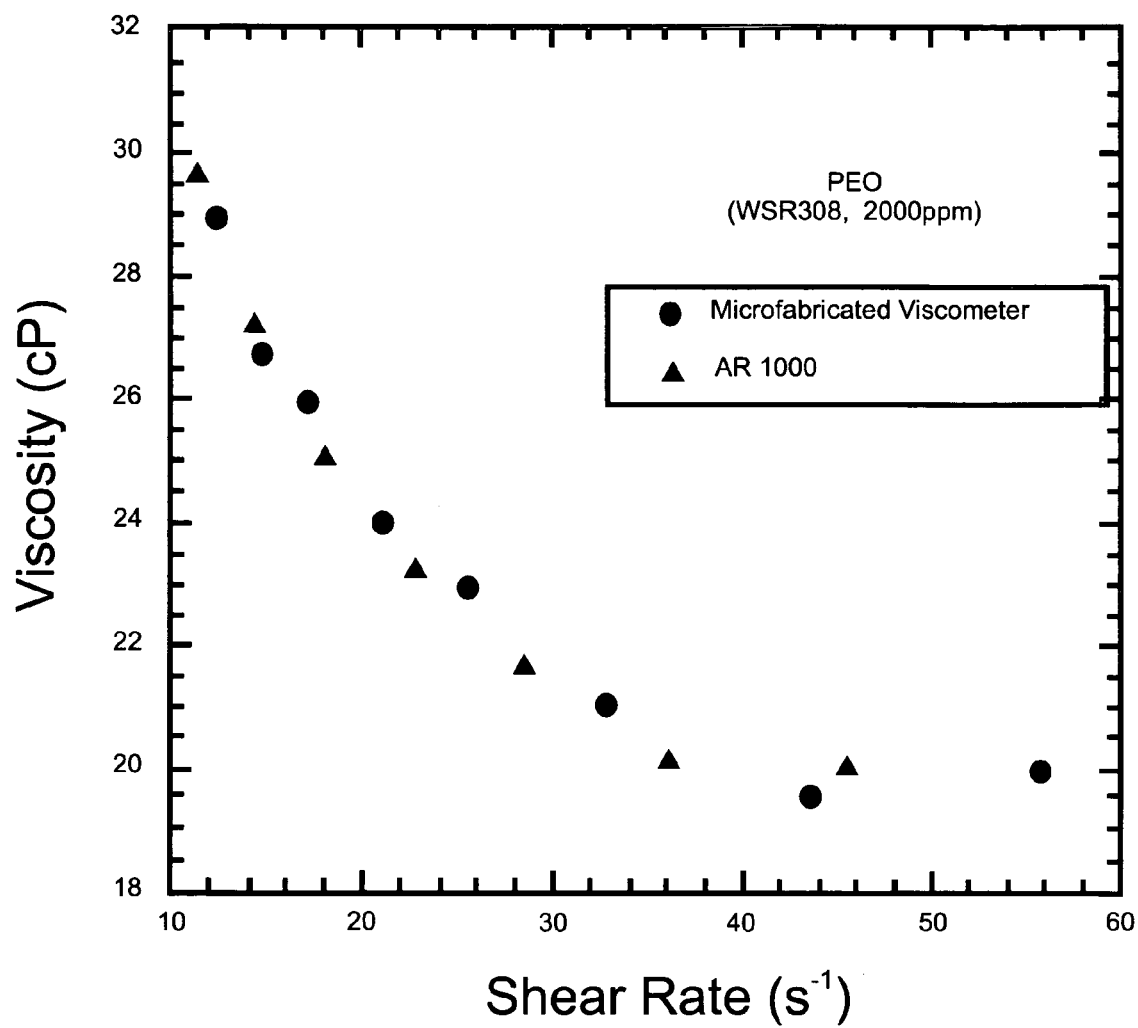
FIG. 13 is a plot of non-Newtonian Viscosity (cP) as a function of Shear Rate (s–1) for a semi-dilute solution of Polyethylene Oxide (PEO, WSR308, 2000 ppm) at 23° C.; for comparison, the corresponding results from the cone and plate viscometer (AR 1000, TA Instruments) are also shown (filled triangles)
Figure 14:
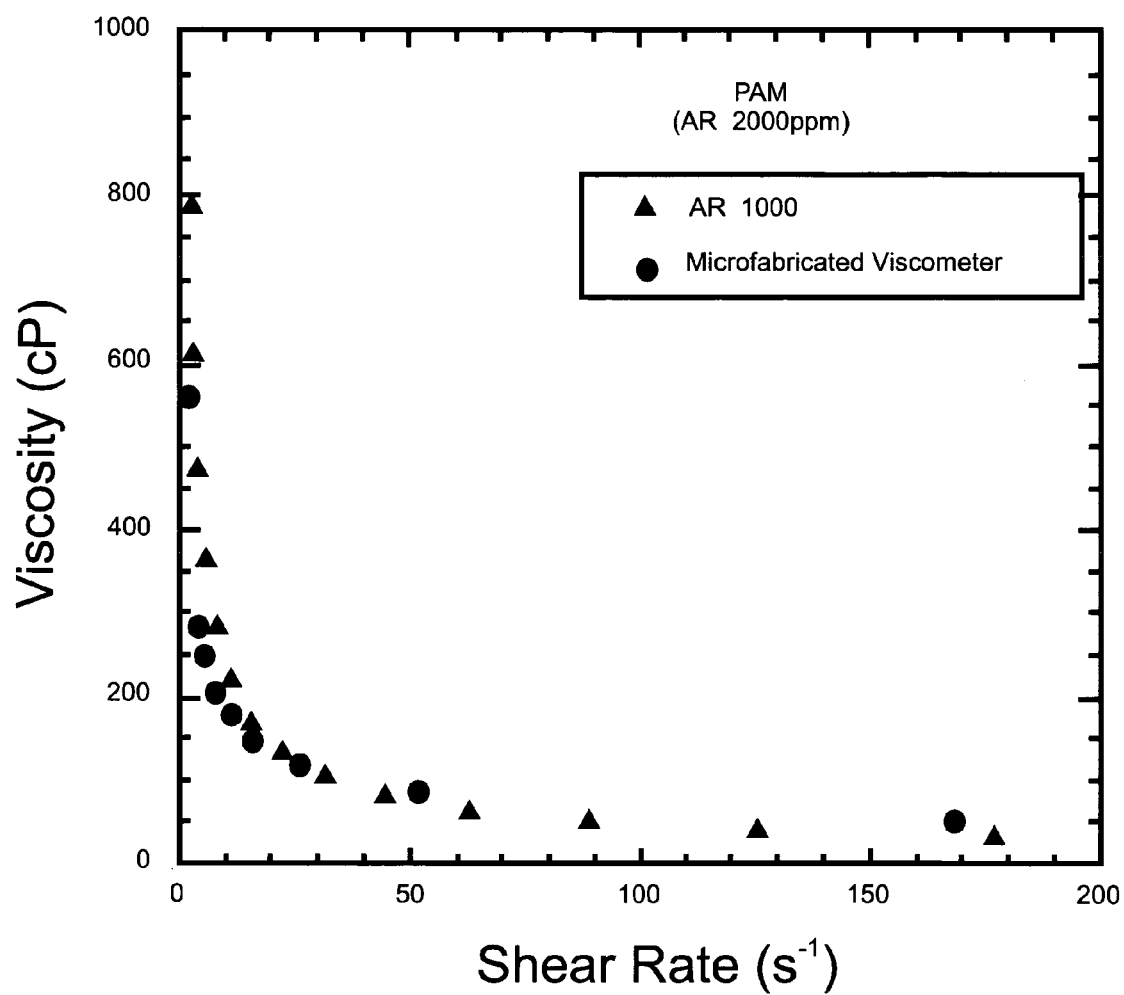
FIG. 14 is a plot of non-Newtonian Viscosity (cP) as a function of shear sate ($s^{-1}$) for a dilute solution of hydrolyzed polyacrylamide (PAM (18% hydrolyzed), AR110, 2000 ppm) at 23° C. For comparison, the corresponding results from the cone and plate viscometer (AR 1000, TA Instruments) are also shown (filled triangles).
Figure 15:
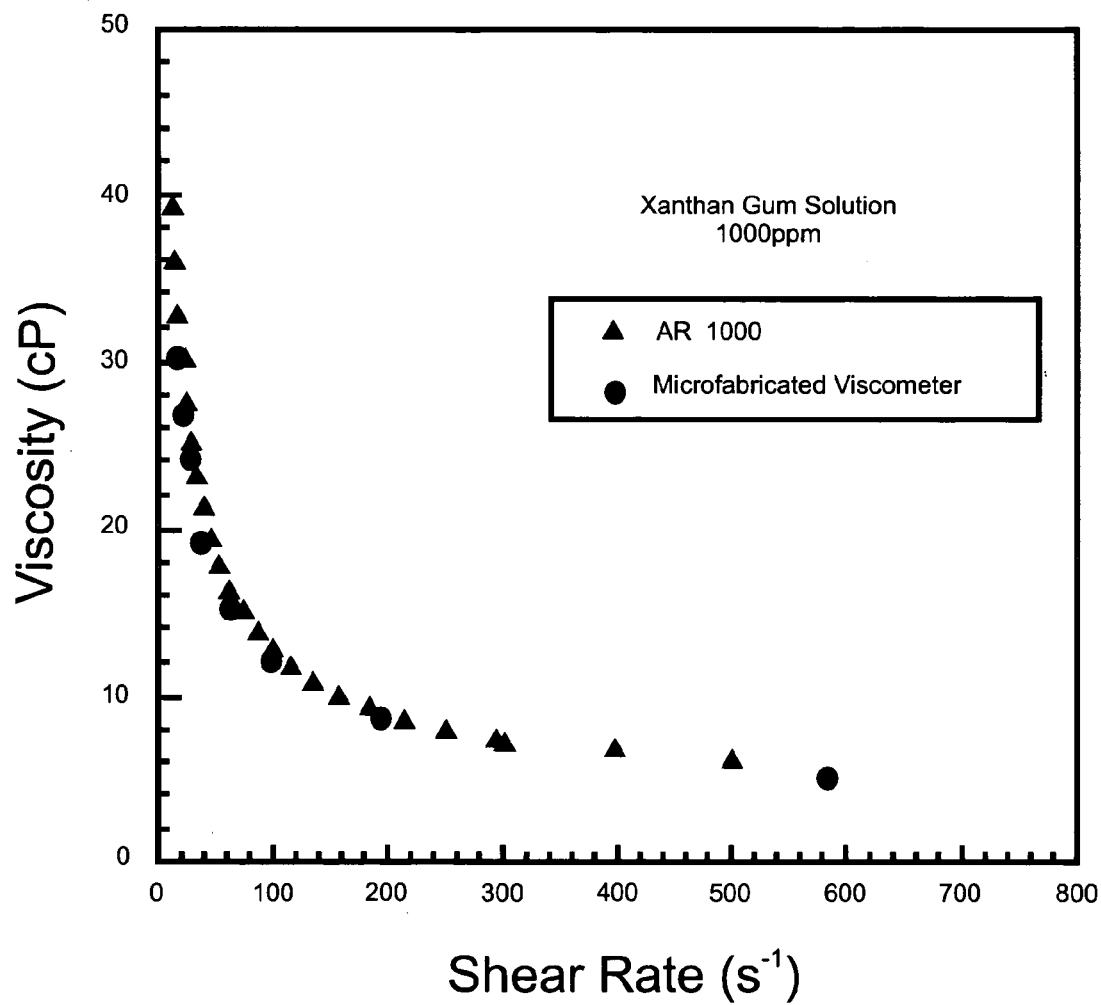
FIG. 15 is a plot of non-Newtonian Viscosity (cP) as a function of Shear Rate ($s^{-1}$) for a 1000 ppm solution of Xanthan Gum at 23° C.; for comparison, the corresponding results from the cone and plate viscometer (AR 1000, TA Instruments) are also shown (filled triangles).

The power law exponent of dilute solution of PEO (500 ppm, as described earlier) is found to be 0.88 and the viscosity as a function of shear rate is shown in FIG. 12. A semi-dilute solution of PEO (WSR308, 2000 ppm) is then tested on the microfabricated viscometer. The power law exponent is found to be 0.75 and the viscosity as a function of shear rate is plotted in FIG. 13. The viscosity of another semi-dilute polymer solution, hydrolyzed PAM (AR110, 2000 ppm) is then tested on the microfabricated viscometer. The power law exponent is found to be 0.55 and the viscosity is shown in FIG. 14. Finally, the viscosity of an aqueous solution of Xanthan Gum (1000 ppm) is tested. The power law exponent is found to be 0.69, which matches well with the literature value of 0.7 and the viscosity as a function of shear rate is plotted in FIG. 15. For each of these polymeric solutions, the viscosity is also measured on the cone and plate viscometer (AR 1000) and there is good agreement between the results from the cone and plate and from the microfabricated viscometer.

Design Considerations

The geometry of the open channel in the microfabricated capillary viscometer is optimized in order to ensure smooth one phase flow of whole blood. For homogenous one-phase flow of blood, it is observed that the microfabricated channels had to be 100 μm or deeper. Shallow channels (d~40 μm) lead to phase separation of whole blood where plasma can be seen evidently adhering to the channel walls while the red blood cells are found collecting along the centerline of the channel which is also the zero shear stress zone. The flow of whole bovine blood is homogenous with deeper rectangular channels (d~100 μm), which is then used in the power law exponent and non-Newtonian viscosity measurements.

III. Automated Viscosity Measurements

A. Materials and Methods

Glass (Channel) Microfabrication

The channels in a self-calibrating viscometer having the configuration set forth above in FIG. 3B are fabricated. Briefly, a thin metal film (500 Å Chrome/4000 Å Gold) is deposited and patterned on annealed glass wafers (Dow Corning Pyrex 7740, 500 μm thick, 10 cm dia). The glass is then etched in hydrofluoric acid (49%) to a desired thickness (rate~7 μm/min). Finally, the photoresist and metal layers are removed and the glass wafer diced on a dicing saw to yield individual glass dies.

Silicon (Electrode, Heaters and Resistive Temperature Detectors (RTD)) Microfabrication Electrodes, resistive heaters and temperature sensors are fabricated on silicon using the lift-off process. A silicon wafer (<100>, 500 μm thick, 10 cm dia) with 1 μm thick thermal oxide layer (University Wafers, South Boston, Mass.) is spin-coated with photoresist (Microposit SC 1827) at 3000 rpm, soft-baked at 90° C. for 5 min and exposed with a mask aligner. The wafer is then developed in MF 319 (Shipley) for 1.5 min followed with a 500 Å Cr/4500 Å gold evaporation. After lift-off in acetone for 5 h, the wafer is diced on a dicing saw to yield individual silicon dies.

Glass—silicon Device Assembly

A custom designed immersion gold printed circuit board (PCB, Advanced Circuits, Aurora, Colo.) serves as the platform for chip-to-world electrical connections. The structure of this printed circuit board is described generally in FIGS. 5 and 6. The diced silicon devices are cleaned (with acetone, IPA, and DI water) and fixed to the PCB using a double stick tape. The gold contact pads on the silicon die are wire bonded (Kulicke & Soffa 4124 Ball Bonder) using 1.0 mil gold wire. After wire bonding, the piranha cleaned glass side component is visually aligned to the silicon side and UV curable optical glue (SK-9, 40 cp, Summers Optical, Fort Washington, Pa.) is wicked between glass and silicon through the edges. The device is cured in UV light (365 nm) for 6 hours.

Microfluidic Method for Measuring Viscosity

The glass-hybrid microfluidic device for measuring dynamic viscosity of a liquid sample is set forth above (FIG. 3B). There are two "open channels" (OC$_1$ and OC$_2$) and two "sealed chambers" (SC$_1$ and SC$_2$). Equation 1 is the primary governing equation that is used for analyzing the laminar flow of liquid and subsequently measuring viscosity, μsample from the flow data. For use in Equation 1, 'vL' is measured on the OC's and 'P$_{capillary}$' is measured on the SC's (described below). One set of OC$_1$ and SC$_1$ measures vL$_{calib}$ and P$_{capillary,calib}$ for a liquid of known viscosity, μ$_{calib}$ while the other set (OC$_2$ and SC$_2$) is used for the sample liquid. Using Equation (1) and knowing that the geometry of OC$_1$ and OC$_2$ is identical (i.e., same d and S), we obtain:

$$\mu_{sample} = \mu_{calib}(vL_{calib}/P_{capillary,calib})P_{capillary,sample}/vL_{sample} \quad (8)$$

The above-derived Equation 8 is then used for calculating the viscosity of an unknown liquid sample.

Measurement of vL

To measure vL, a 5 μL drop of solution (e.g., water) is placed at the inlet of the open channel (OC) and is spontaneously drawn in by capillary pressure. While the liquid is in motion, the length of the liquid column inside the channel, L, is monitored as a function of time. The incremental increase in the length (ΔL) over short times (Δt) is used to calculate the velocity (i.e., v=ΔL/Δt). Using this data of L and v, the product is then calculated at different locations inside the viscometer. vL is largely constant throughout the channel and a simple mean value is computed.

Measurement of Capillary Pressure. P$_{capillary}$ is measured on the sealed chamber (SC's) that has a single inlet and no outlet. A drop of liquid placed at the inlet of the SC is spontaneously drawn in compressing the trapped air inside the chamber. The air pressure in the chamber now exceeds the atmospheric pressure by an amount equal to the capillary pressure. As set forth above, utilization of the ideal gas law provides equation 6:

$$P_{capillary} = P_{atm}(V_1/V_2 - 1) \qquad (6)$$

where $V_1$ is the original volume of air inside the chamber and $V_2$ is the volume of the compressed air found from the position of the static liquid meniscus inside the chamber.

Liquid Detection using on-chip gold microelectrodes

A change of electrical conductance is used to detect the presence of a liquid droplet over a microelectrode inside the device. The change in electrical conductance is measured by applying a DC electrical signal (2.7V) to a pair of on-chip electrodes, which is in series with an external resistor. The voltage response from these resistors is continuously monitored using LabVIEW™ and may be divided into three specific regions. In the absence of any liquid inside the channel, there is no conduction path between the electrodes and thus no electric current flows through the circuit (Region 1). However, as soon as the liquid passes over the electrodes, a conduction path is set up. As a result, an electric current flows through the circuit and a non-zero voltage drop across the resistor is observed (Region 2). Once the presence of the liquid is detected, the time at which this change occurred is saved and the voltage supply to the electrodes is turned off immediately (Region 3).

Data Acquisition using Labview™

The setup for automated portable measurement of viscosity consists of a DC power supply (hp 6234A, American Test Equipment, Ashland, Va.), a data acquisition card (DAQ-Card™-AI-16XE-50 with CB-68 LP board, National instruments, Austin, Tex.), one digital relay board (ER-16, National Instruments), a laptop computer (Macintosh, Apple Computer Inc) and LabVIEW™ control program (National Instruments). Edge connectors from the PCB connect each pair of on-chip electrode in series with a 10 MW external resistor; one of the electrodes in each pair is grounded while the other is connected to the power supply. The voltage drop across the 10 MW resistor is fed to the Labview VI (National Instruments, TX) using the analog input of the DAQ board. The scanning rate is 100,000 samples per sec and averaging a sample of 1000 samples.

Use of Feedback Controlled Digital Relays to Avoid Electrolysis

Due to the use of DC voltage (2.7V) for operation that is above the electrolytic voltage of water (1.23V), there might be formation of hydrogen and oxygen. In order to prevent electrolysis and bubbling of liquid due to prolonged exposure to a DC electric field, the power to the microelectrodes is controlled through a digital relay board (ER-16). These digital relays shut the power off selectively to a pair electrode as soon as liquid has been detected over it. As a result, any droplet of liquid will not experience the electric field for more than 0.3 s—(the rate at which each pair of electrode is scanned by Labview) and hence prevent electrolysis.

B. Results

Automated Operation of the Self-Calibrating Nanoliter Viscometer

The automated viscometer set forth above is used to measure vL using on-chip gold microelectrodes as described in FIGS. 6A and 6B. A control program in LabVIEW™ calculates vL based on the real time data that it obtains from the eight pairs of electrodes, e1 through e8 located in the open channel. The distance of each pair of electrode from the inlet of the channel 11 through 18, is known from design (Table 2).

TABLE 2

| Distance from the inlet of the open channel (cm) | |
| --- | --- |
| $l_1$ | 2.47 |
| $l_2$ | 3.21 |
| $l_3$ | 3.96 |
| $l_4$ | 4.7 |
| $l_5$ | 5.44 |
| $l_6$ | 6.19 |
| $l_7$ | 6.93 |
| $l_8$ | 7.67 |

Figure 16A:
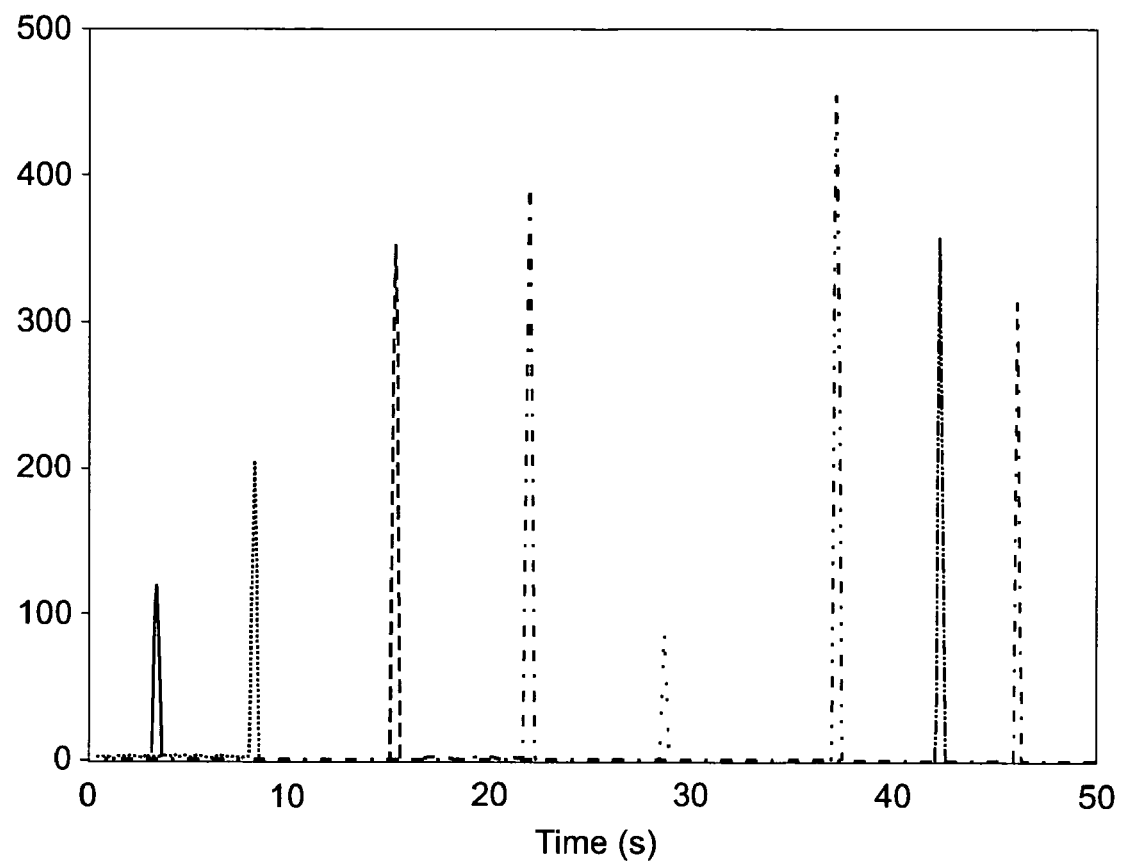
FIG. 16A is a plot of the real-time response from the eight electrodes in the open channel as liquid passes over a given pair electrode (the power to the electrode is turned off when a peak in voltage from that electrode is detected and the time for this peak is used to calculate the viscosity)

To measure vL, a DC voltage of 2.7V is applied to the eight pairs of electrodes and next, a 10 μL drop of liquid is added to the open channel. As the drop flows over a pair of electrodes, a non-zero voltage is detected from that electrode pair. FIG. 16A shows the peak voltage response from the eight electrodes as the liquid flows through the channel. The time, t of the peak from each pair of electrode is recorded and knowing the distance of each electrode from the inlet, the length of the liquid droplet, L is plotted with t. From the data of L with t, the real time velocity of the liquid droplet, v ($v = \Delta L/\Delta t$) is computed. An average value of vL is then calculated using the data on L and v at the eight locations.

Figure 16B:
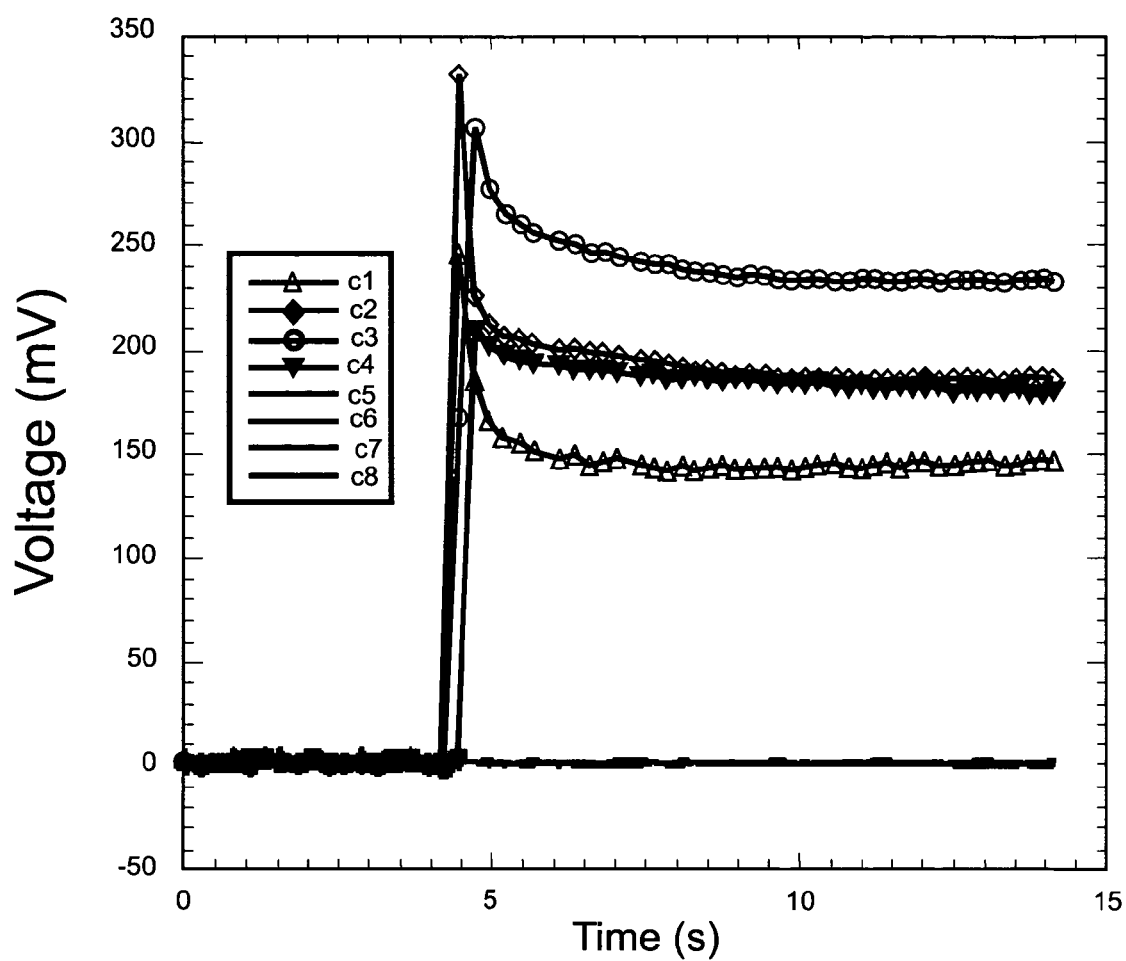
FIG. 16B is a plot of the voltage response from eight pairs of electrodes an open channel as shown in FIG. 6A.

The control program in LabVIEW™ measures $P_{capillary}$ using the sealed chamber (SC) and employing Equation (8). FIGS. 6A and 6B show the arrangement of electrodes for measuring $V_2$ and thus $P_{capillary}$; eight electrodes, c1 through c8, protrude into the inlet channel of the sealed chamber while a common long electrode (c1e1) runs all along the inlet channel. To measure $P_{capillary}$, a drop of liquid is added to the sealed chamber. After allowing sufficient time (~10 s) for the liquid to attain the equilibrium static meniscus inside SC, a DC voltage of 2.7 V is applied to c1e1 while c1 through c8 are grounded. The voltage response from the eight electrodes, c1 through c8, is indicative of the length of the static liquid droplet. Knowing the cross-sectional area of the channel, the volume of the liquid drop and $V_2$ is then calculated. FIG. 16B shows the voltage response from the eight electrodes for a drop of water and the corresponding optical micrograph. The volume of the droplet ($V_1-V_2$) in this case is measured in LabVIEW™ to be 42 nL corresponding to the volume between the inlet of the channel and last electrode with a non-zero voltage response (electrode # c4 in this case). In this case water is found to be 1615 Pa.

The viscometer system shown in FIG. 6 is successfully used to measure the viscosity of water—the total time for operation including setting up the device, on-chip calibration, adding the liquid sample and obtaining an electronically displayed viscosity value is 4 minutes. First, the vL and $P_{capillary}$ for the calibration liquid (D1.2 Viscosity standard, Paragon Medical) using $OC_1$ and $SC_1$ is measured and found to be 1.23 cm2/s and 1615 Pa respectively. Next, water is added to $OC_2$ and $SC_2$ and $P_{capillary}$ is calculated from the response of the electrodes in $SC_2$. LabVIEW™ then calculates and displays a viscosity value as soon as water passes over the 2nd electrode (e2) and is based on the time it took to travel from e1 to e2 in $OC_2$. The viscosity value is updated as water flows over the 3rd, 4th, 5th, 6th, 7th and 8th electrode. This real time measurement of viscosity is determined with LabVIEW. The seventh and final viscosity is found to be 1.02 cP at 23° C. The measured viscosity of water compares favorably with both the literature value of 0.981 cP as well as with the measurements on a commercial cone and plate viscometer (AR1000 Rheometer).

Design Considerations and Alternative Nanoliter Droplet Detection Methods

An on-chip liquid detection system in accordance with FIGS. 4, 5, and 6 is constructed. The on-chip liquid detection system consists of an array of 100 µm thick gold microelectrodes located inside the open channels and sealed chambers. The liquid flows inside by capillary pressure and the electrodes transmit real time data on the position of the advancing liquid interface in the open channel and on the static liquid interface in the sealed chamber. This real time data is translated into vL and $P_{capillary}$ and finally into a real time viscosity, $\mu_{sample}$ as set forth above.

The effect of gold microelectrodes on the surface of the microchannels, in particular on the capillary pressure measurement is investigated. While the liquid encounters electrodes only at few points inside the open channel (OC), the density of electrodes is much higher in the inlet to the sealed chamber (SC). Since the capillary pressure found from the SC is assumed to be the same as the capillary pressure driving liquid flow in the OC, it is critical to ensure that the surface is equally affected or unaffected by the presence of microelectrodes in OC and SC. For this purpose, control devices that had gold microelectrodes in one sealed chamber ($SC_1$) and none on the other ($SC_2$) are fabricated (device not shown). A 10 µl drop of water is added to both $SC_1$ and $SC_2$ and the capillary pressure is measured. These control experiments did not reveal any change in the capillary pressure due to the addition of microelectrodes. However, it is noticed that the shape of the static meniscus over the electrodes is sometimes distorted; there is less wetting on the common gold electrode. In such cases, volume corresponding to the leading meniscus, shown with a dotted line, is used in the measurement of capillary pressure.

Figure 17:
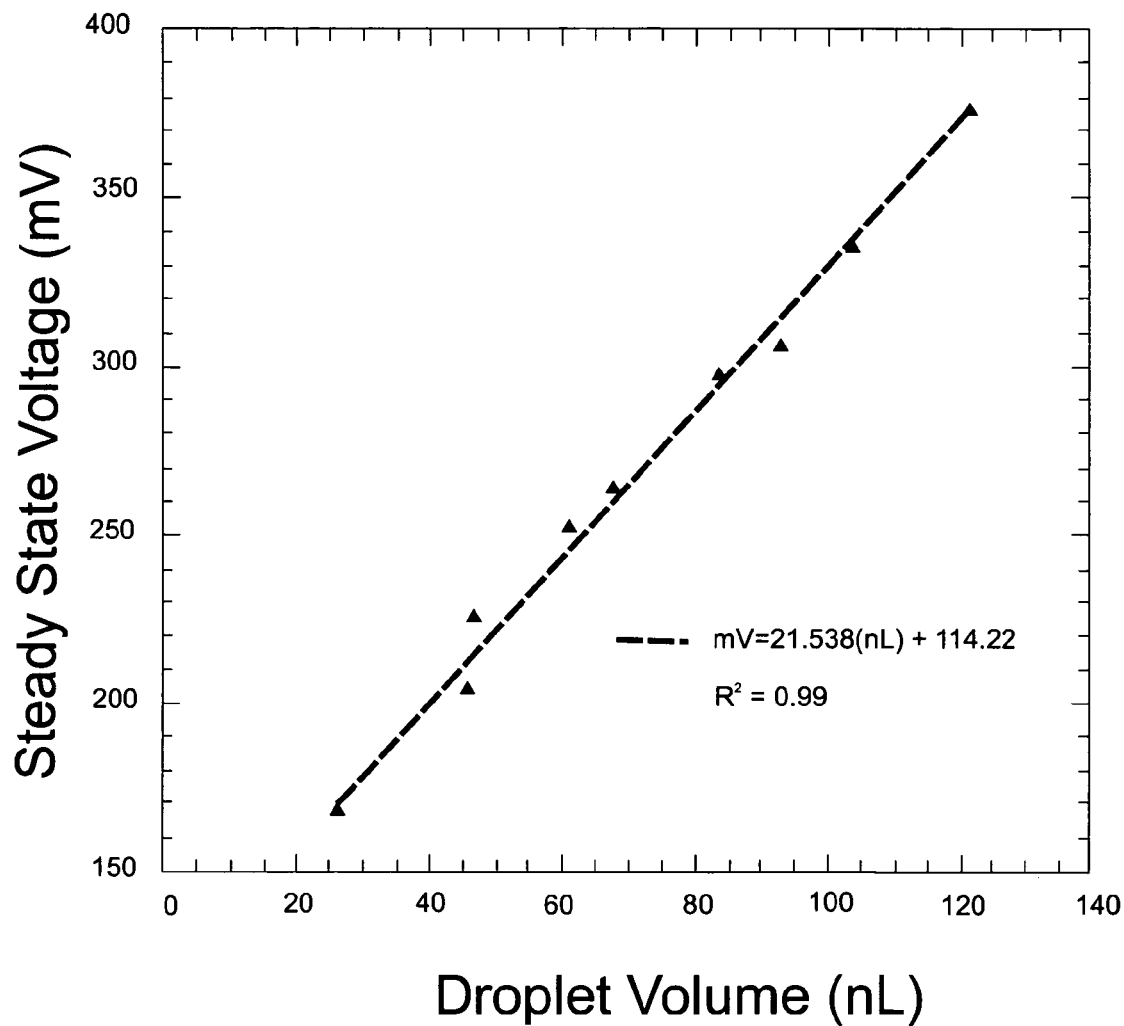
FIG. 17 is a plot of the steady state voltage response (mV) vs. droplet volume (nL) for water inside the device of FIG. 7.

The "analog" detection method of FIG. 7 is tested on a microfluidic device containing a side channel and two parallel gold microelectrodes that run all along the channel. The side channel is 400 µm wide and the microelectrodes are 100 µm wide and 100 µm apart. A drop of water is added at the inlet and is carefully placed so that it only partially wetted the pair of electrodes. About 3 Volts DC is then applied across the electrodes and the steady state voltage response from the electrodes is recorded. In experiments, the volume of water droplet over is carefully varied and similar voltage measurements are made for each volume of droplet. The plot of the steady state voltage response from the microelectrodes as a function of the droplet volume is shown in FIG. 17. It appears that the voltage response from the electrodes increases linearly as the volume of the liquid droplet.

Finally, a thermal method of detecting the presence of nanoliter droplets inside a microfluidic channel as set forth above is investigated. A device that contains channels in glass and metal heaters and temperature sensors on the silicon is constructed. A droplet of water is added from the inlet and moved towards the right using short duration (11 ms) pulses of air pressure (8 psi). The droplet destination is obtained using electronic data from the resistive temperature detectors (RTD) that are located beneath the fluidic channels. The device is locally heated at the destination to 350 C by supplying 27V to the metal heater and the voltage output from the RTD is continuously monitored. The presence of droplets is sensed by the RTD through a local change.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A viscometer for determining the viscosity of a liquid, the viscometer comprising:
a first substrate having a first channel-defining surface;
a second substrate having a second channel-defining surface;
a first channel defined by the first and second channel-defining surfaces, the first channel having an inlet for introduction of liquid into the first channel and an outlet for venting gas as liquid fills the first channel; and
a liquid rate measuring meter for measuring the rate at which liquid fills the first channel, the liquid rate measuring meter in communication with the first channel wherein the rate at which liquid fills the first channel is used to determine the viscosity; and
a data processing system for calculating the viscosity of a liquid, the data processing system operable to calculate the viscosity, µ, using formula 2:

$$\mu = (d^2/S)(\Delta P/vL) \quad (2)$$

wherein v is the mean velocity, d is the depth of the channel, L is the length of the liquid column inside the channel at any time, µ is the liquid viscosity, $\Delta P$ is the pressure difference across liquid inside the first channel, and S is the shape factor.

2. The viscometer of claim 1 wherein the first substrate is a glass plate and the first channel-defining surface is a trench positioned in the glass plate.

3. The viscometer of claim 2 wherein the second substrate is a silicon wafer, the glass plate positioned over the silicon wafer such that the glass plate in combination with the silicon wafer define the first channel.

4. The viscometer of claim 1 wherein the cross-sectional area of the first channel is such that the liquid flow is driven by capillary pressure.

5. The viscometer of claim 4 wherein the cross-sectional area of the first channel is from about 0.003 mm² to about 0.05 mm² and the length of the first channel is from about 10 mm to about 200 mm.

6. The viscometer of claim 1 further comprising a data acquisition system operable to receive information regarding the amount of liquid within the first channel as a function of time.

7. The viscometer of claim 1 wherein the data processing system is operable to calculate the $\Delta P$ using formula 3:

$$\Delta P = P_1 - P_2 = (P_{atm} - \sigma/R2) - (P_{atm} - \sigma/R_1) = \sigma/R_2 \quad (3)$$

wherein:
$P_1$ is external pressure,
$P_2$ is pressure inside the first channel,
$1/R_2$ is $2 \cos \theta (1/d + 1/w)$,
$\theta$ is the contact angle,
$\sigma$ is the surface tension of the liquid, and
w is the width of the channel.

8. The viscometer of claim 1 wherein data processing system is operable to determine viscosity for a non-Newtonian liquid by determining power n from equation:

$$\tau = \eta Y = mY^n \quad (11)$$

and viscosity, $\eta$ from equation:

$$\eta = mY^{n-1} \quad (10)$$

wherein:
η is the viscosity of a non-Newtonian liquid;
n and m are constants characterizing the fluid flow;
Y is the shear rate; and
τ is the shear stress.

9. The viscometer of claim 8 wherein the shear rate Y is measurable from values of about 20/s to about 500/s.

10. The viscometer of claim 1 further comprising:
a second channel defined by a third channel-defining surface and a fourth channel-defining surface, the second channel having an inlet for introduction of liquid into the second channel but no outlet for venting gas; and
a volume meter for measuring the amount of liquid filling the second channel in order to determine the pressure driving flow of liquid in the first channel, the volume meter in communication with the second channel;
wherein the first substrate further comprises the third channel defining surface and the second substrate further comprises the fourth substrate defining surface and the pressure driving the flow of liquid in the first channel is used to determine the viscosity of the liquid.

11. The viscometer of claim 10 wherein the data processing system is operable to calculate the ΔP using formula 6:

$$P_{capillary} = P_{atm}(V_1/V_2 - 1) \tag{6}$$

wherein:
ΔP equals $P_{capillary}$;
$V_1$ is the initial volume of air inside the second channel before liquid is introduced; and
$V_2$ is the volume of the compressed air found from the position of the air/liquid meniscus inside the second channel after liquid is introduced.

12. The viscometer of claim 10 further comprising a third channel that is substantially the same as the first channel and a fourth channel that is substantially the same as the second channel, the third channel and forth channel operable to be used for calibration of the viscosity determined with the first and second channels.

13. A viscometer for determining the viscosity of a liquid comprising:
a first substrate having a first channel-defining surface and a third channel-defining surface;
a second substrate having a second channel-defining surface and a fourth channel-defining surface;
a first channel defined by the first and second channel-defining surfaces, the first channel having a first inlet for introduction of liquid into the first channel and a first outlet for venting gas as liquid fills the first channel; and
a second channel defined by the third channel-defining surface and the fourth channel-defining surface, the second channel having an inlet for introduction of liquid into the second channel but no outlet for venting gas, the second channel having a closed or sealed end;
a liquid rate measuring meter for determining the rate at which liquid fills the first channel, the liquid rate measuring meter in communication with the first channel;
a volume meter for measuring the amount of liquid filling the second channel in order to determine the pressure driving flow of liquid in the first channel, the volume meter in communication with the second channel;
wherein the rate at which liquid fills the first channel and the pressure driving the flow of liquid in the first channel is used to determined the viscosity of the liquid;
a third channel that is substantially the same as the first channel; and
a fourth channel that is substantially the same as the second channel, the third channel and fourth channel operable to be used for calibration of viscosity determined with the first and second channels.

14. The viscometer of claim 13 wherein the first substrate is a glass plate and the first channel-defining surface is a trench positioned in the glass plate, and the second substrate is a silicon wafer, the glass plate positioned over the silicon wafer such that the glass plate in combination with the silicon wafer define the first channel.

15. The viscometer of claim 13 further comprising a data acquisition system in communication with the liquid rate measuring meter and the liquid volume meter; and a data processing system for calculating the viscosity of a liquid.

16. The viscometer of claim 13 wherein the data processing system is operable to calculate the viscosity, μ, using formula 2:

$$\mu = (d^2/S)(\Delta P/vL) \tag{2}$$

wherein v is the mean velocity, d is the depth of the channel, L is the length of the liquid column inside the channel at any time, μ is the liquid viscosity, ΔP is the pressure difference across liquid inside the first channel, and S is a shape factor.

17. The viscometer of claim 16 wherein the data processing system is operable to calculate the ΔP using formula 3:

$$\Delta P = P_1 - P_2 = (P_{atm} - \sigma/R_1) - (P_{atm} - \sigma/R2) = \sigma/R_2 \tag{3}$$

wherein:
$P_1$ is external pressure,
$P_2$ is pressure inside the first channel,
$1/R_2$ is 2 cos θ(1/d+1/w),
θ is the contact angle,
σ is the surface tension of the liquid, and
w is the width of the channel.

18. The viscometer of claim 16 wherein the data processing system is operable to determine the power n from equation:

$$\sigma = \eta Y = mY^n$$

and the viscosity, η from equation:

$$\eta = mY^{n-1}$$

wherein:
η is the viscosity of a non-Newtonian liquid;
n and m are constants characterizing the fluid flow; and
where τ is the shear stress.

19. The viscometer of claim 13 wherein the data processing system is operable to calculate the ΔP using formula 6:

$$P_{capillary} = P_{atm}(V_1/V_2 - 1) \tag{6}$$

wherein:
ΔP equals $P_{capillary}$;
$V_1$ is the initial volume of air inside the second channel before liquid is introduced; and
$V_2$ is the volume of the compressed air found from the position of the air/liquid meniscus inside the second channel after liquid is introduced.

20. A method of measuring the viscosity of a liquid, the method comprising:
measuring the rate at which the liquid fills a first channel, the first channel being defined by a first channel-defining surface in a first substrate and a second channel-defining surface in a second substrate wherein the first channel has an inlet for introduction of liquid into the first channel and an outlet for venting gas as liquid fills the first channel;

determining the pressure that drives the liquid as it flows in the first channel; and calculating the viscosity of the liquid from formula 2:

$$\mu = (d^2/S)(\Delta P/vL) \quad (2)$$

wherein v is the mean velocity, d is the depth of the channel, L is the length of the liquid column inside the channel at any time, $\mu$ is the liquid viscosity, $\Delta P$ is the pressure difference across liquid inside the first channel, and S is a shape factor.

21. The method of claim 20 wherein the $\Delta P$ is given by formula 3:

$$\Delta P = P_1 - P_2 = (P_{atm} - \sigma/R_1) - (P_{atm} - \sigma/R2) = \sigma/R_2 \quad (3)$$

wherein:
$P_1$ is external pressure,
$P_2$ is pressure inside the first channel,
$1/R_2$ is $2 \cos \theta (1/d + 1/w)$,
$\theta$ is the contact angle,
$\sigma$ is the surface tension of the liquid, and
w is the width of the channel.

22. The method of claim 20 wherein the viscosity is determined by calculating power n from equation:

$$\tau = \eta Y = m Y^n$$

and the viscosity, $\eta$ from equation:

$$\eta = m Y^{n-1}$$

wherein:
$\eta$ is the viscosity of a non-Newtonian liquid;
n and m are constants characterizing the fluid flow; and
where $\tau$ is the shear stress.

23. The method of claim 20 further comprising:
measuring the amount of liquid that fills a second channel, the second channel being defined by a third channel-defining surface in the first substrate and a fourth channel-defining surface in the second substrate; and
wherein the first substrate further comprises the third channel defining surface and the second substrate further comprises the fourth substrate defining surface and the pressure driving the flow of liquid in the first channel is used to determined the viscosity of the liquid;
wherein is calculated the $\Delta P$ using formula 6:

$$P_{capillary} = P_{atm}(V_1/V_2 - 1) \quad (6)$$

wherein:
$\Delta P$ equals $P_{capillary}$;
$V_1$ is the initial volume of air inside the second channel before liquid is introduced; and
$V_2$ is the volume of the compressed air found from the position of the air/liquid meniscus inside the second channel after liquid is introduced.

* * * * *

UNITED STATES PATENT AND TRADEMARK OFFICE
CERTIFICATE OF CORRECTION

PATENT NO. : 7,188,515 B2  Page 1 of 1
APPLICATION NO. : 11/235641
DATED : March 13, 2007
INVENTOR(S) : Mark A. Burns et al.

It is certified that error appears in the above-identified patent and that said Letters Patent is hereby corrected as shown below:

Column 22, Line 51, Claim 7:

Delete:

$$\Delta P = P_1 - P_2 = (P_{atm} - \sigma/R2) - (P_{atm} - \sigma/R_1) = \sigma/R_2 \qquad (3)$$

and insert therefor:

$$\Delta P = P_1 - P_2 = (P_{atm} - \sigma/R_1) - (P_{atm} - \sigma/R2) = \sigma/R_2 \qquad (3)$$

Signed and Sealed this

Twenty-fifth Day of March, 2008

JON W. DUDAS
*Director of the United States Patent and Trademark Office*